(12) United States Patent
Pfeffer et al.

(10) Patent No.: US 8,193,175 B2
(45) Date of Patent: Jun. 5, 2012

(54) RUTHENIUM COMPLEXES FOR TREATING CANCERS

(75) Inventors: Michel Pfeffer, Strasbourg (FR); Claude Sirlin, Bischeim (FR); Jean-Philippe Loeffler, Berstett (FR); Christian Gaiddon, Strasbourg (FR); Pierre Bischoff, Guebwiller (FR); Pierre Jeannequin, Strasbourg (FR)

(73) Assignee: Universite de Strasbourg, Strasbourg Cedex (FR)

( * ) Notice: Subject to any disclaimer, the term of this patent is extended or adjusted under 35 U.S.C. 154(b) by 1536 days.

(21) Appl. No.: 11/631,979

(22) PCT Filed: Jul. 13, 2005

(86) PCT No.: PCT/FR2005/001814
§ 371 (c)(1),
(2), (4) Date: Jan. 9, 2007

(87) PCT Pub. No.: WO2006/016069
PCT Pub. Date: Feb. 16, 2006

(65) Prior Publication Data
US 2008/0051370 A1    Feb. 28, 2008

(30) Foreign Application Priority Data
Jul. 13, 2004 (FR) .................... 04 07819

(51) Int. Cl.
*A61K 31/555* (2006.01)
*C07F 15/00* (2006.01)
(52) U.S. Cl. ........................ 514/185; 546/10
(58) Field of Classification Search ................. 514/185; 546/10
See application file for complete search history.

(56) References Cited

FOREIGN PATENT DOCUMENTS
WO 97/36595 10/1997
WO 00/56743 9/2000

OTHER PUBLICATIONS

International Search Report for PCT/FR05/01814 mailed Jan. 20, 2006 (English and French).

Ryabov et al., *New synthesis and new bio-application of cyclometalated ruthenium(II) complexes for fast mediated electron transfer with peroxidase and glucose oxidase*, Inorganic Chemistry, Dec. 3, 2001, vol. 40, No. 25, pp. 6529-6532, XP002317880.

Database CA 'Online!, Chemical Abstracts Service, Accession No. 2003:210594 (1999),Davydova et al., *Stability and catalytic properties of glucose oxidase from Penicillium funiculosum G-15 Electrophilic Substitution Reactions at the Phenyl Ring of the Chelated 2-(2'-Pyridyl)phenyl Ligand Bound to Ruthenium(II) or Osmium (II)*, XP002359467.

Le Lagadec et al., *Cyclometalated N,N-dimethylbenzylamine ruthenium(II) complexes 'Ru(C6HR1R2R3-o-CH2NMe2)(bpy)(RCN)2!PF6 for bioapplications: synthesis, characterization, crystal structures, redox properties, and reactivity toward PQQ-dependent glucose dehydrogenase*, Journal of Organometallic Chemistry, 689(25), 4820-4832, 2004, XP002317879.

Ryabov et al., *Redox Mediation and Photomechanical Oscillations Involving Photosensitive Cyclometalated Ru(II) Complexes, Glucose Oxidase, and Peroxidase*, Analytical Chemistry, 77(4), 1132-1139, (2005) XP002359422.

Clark et al., *Electrophilic Substitution Reactions at the Phenyl Ring of the Chelated 2-(2'-Pyridyl)phenyl Ligand Bound to Ruthenium(II) or Osmium(II)*, Organometallics, 18(15), 2813-2820, (1999) XP002359423.

Ritleng et al., *Reaction between Ethylene and Cycloruthenated Tertiary Amines: Stoichiometric Olefin Arylation and Stereospecific One-Carbon-Atom Insertion*, Organometallics, 22(2), 347-354, (2003) XP002317878.

Perez et al., *Synthesis and Structure of the First Ruthenated Benzodiazepines*, Organometallics, 21(24), 5437-5438, (2002) XP002317881.

Flower et al., *Synthesis and Characterization of Cycloruthenated (2-(Phenylimino)phenyls: A Useful Probe for the Elucidation of the Tautomeric Process in 2-Hydroxphenyl-Schiff Bases*, Organometallics, 21(6), 1184-1189, (2002) )XP002317882.

Database CA 'Online!, Chemical Abstracts 2003:210673 (2002), Ivanova et al., *Enzyme-substrate interactions in oxidation of (+)- and (−)-'Ru(phpy)(phen)2!FP6 by hydrogen peroxide in the presence of horseradish peroxidase*, XP002317883.

Dupont et al, "The Potential of Palladacycles: More Than Just Precatalysts", Chemical Reviews 2005, 105, 2527-2571.

Djukic et al, "Cycloruthenated Compounds—Synthesis and Application", Eur. J. Inorg. Chem. 2009, 817-853.

*Primary Examiner* — Charanjit Aulakh
(74) *Attorney, Agent, or Firm* — Nixon & Vanderhye P.C.

(57) ABSTRACT

The invention concerns uses or methods for treating proliferative pathologies, in particular cancers, using ruthenium compounds and compositions containing the same. The invention also concerns novel ruthenium compounds, as well as their preparation method.

23 Claims, 15 Drawing Sheets cells A 172

Figure 8:
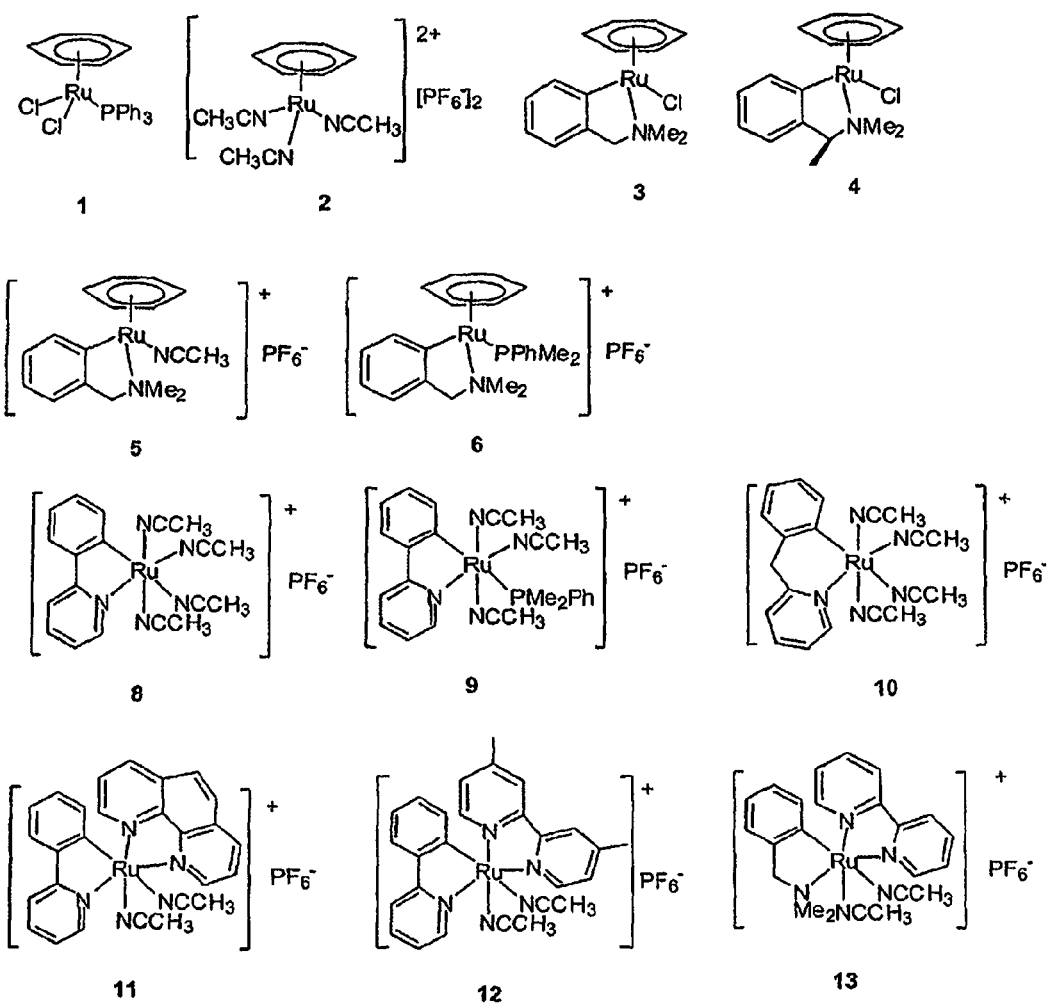

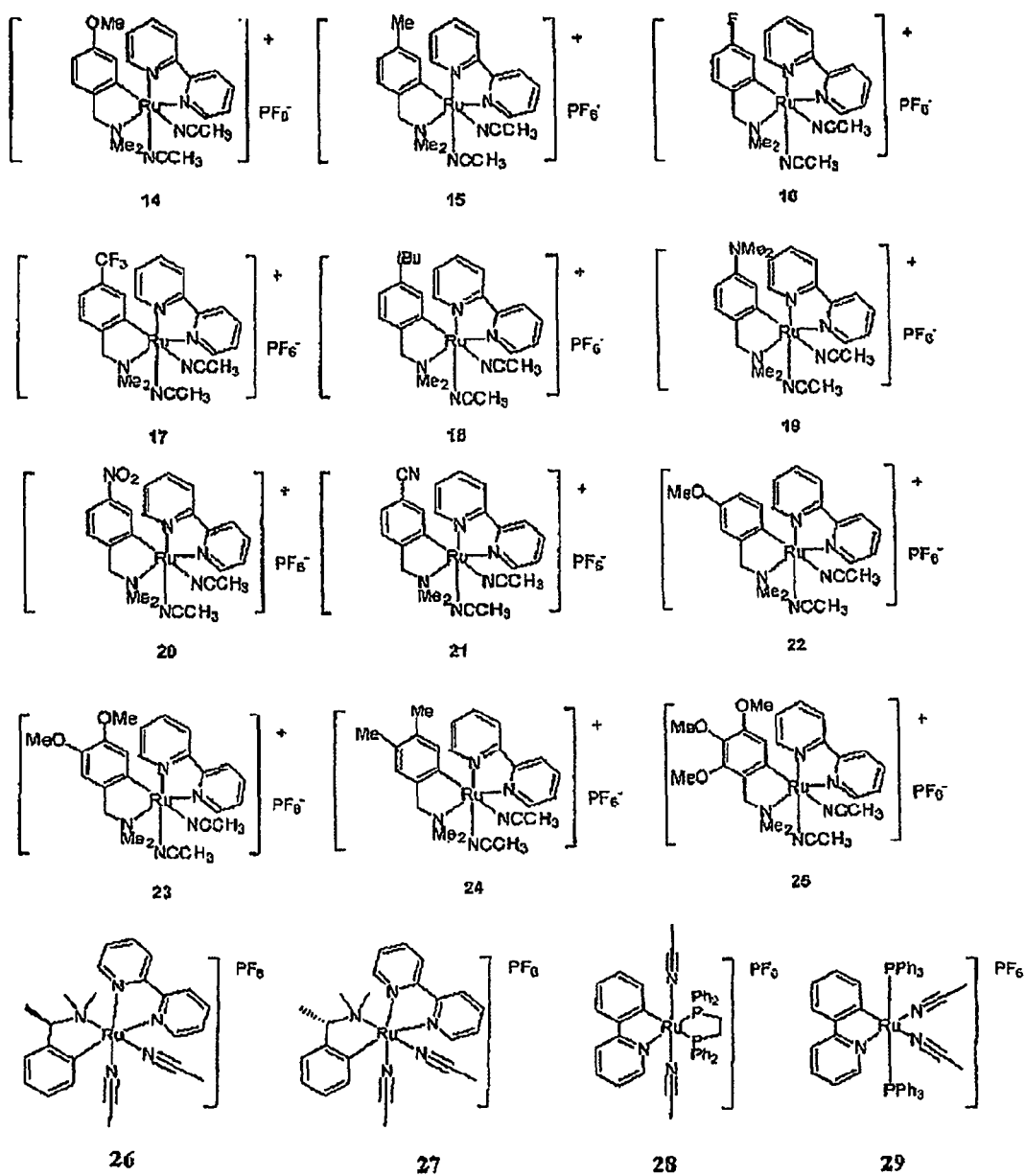
FIGURE 8 (suite)

RUTHENIUM COMPLEXES FOR TREATING CANCERS

This application is the US national phase of international application PCT/FR2005/001814 filed 13 Jul. 2005, which designated the U.S. and claims benefit of FR 0407819, filed 13 Jul. 2004, the entire contents of each of which are hereby incorporated by reference.

The present invention concerns uses or methods for treating proliferative pathologies, in particular cancers, using ruthenium compounds and compositions containing the same. The invention also concerns novel ruthenium compounds, as well as their preparation method.

It is known that metallic compounds containing platinum show significant antitumoral activities. The best known of them is cisplatinum which is currently used for the clinical treatment of numerous cancers. The resistance of certain cancerous cells and the intrinsic toxicity of platinum form part of the problems encountered when using this compound. Since the 1970s, research has been intensified in order to find molecules capable of being substituted for cisplatinum and for several years compounds containing ruthenium have appeared as a possible interesting alternative to those containing platinum. Certain ruthenium complexes have therefore already been described as being a possible alternative in anticancer treatments.

There is therefore a need for novel anticancer agents which could be an alternative to those currently used and/or which would have minimal undesirable side effects.

Therefore, the present invention proposes ruthenium compounds which have particularly beneficial antitumoral properties. These compounds are organometallic compounds, i.e. they contain at least one covalent Carbon-Ruthenium (C—Ru) bond. In addition, this C—Ru bond is stabilised by an intramolecular nitrogen-ruthenium (N—Ru) bond, nitrogen being an element of the organic part bonded to the metal by the carbon atom, in accordance with the following diagram:

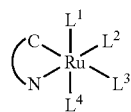

In this type of atom arrangement, ruthenium therefore forms part of a cyclic entity and this class of compounds is generally called the cyclometallised compound class by chemists working in this discipline. The cyclic entity containing ruthenium is called a metallocycle. In a metallocycle, the metal is therefore bonded both to an organic ligand by a covalent carbon-metal bond and a donor-acceptor type nitrogen-metal bond (Lewis acid base, or coordination bond). The existence of a metallocycle in an organometallic molecule gives the latter particular properties in terms of reactivity and thermodynamic stability. Various types of carbon (aromatic, benzylic or aliphatic) can be metallised and the nature of the bond between the donor atom (nitrogen) and carbon can be modified in a plurality of ways.

According to a first aspect, the object of the present invention is therefore a pharmaceutical composition comprising, in a pharmaceutically acceptable support, at least one complex ruthenium compound (II) with the following general formula (I) or (II):

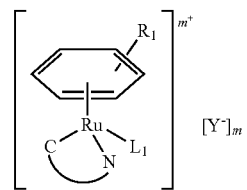

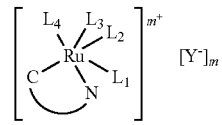

formula (I) or (II) in which:
$L_1$, $L_2$, $L_3$ and $L_4$, identical or different, represent either a donor ligand with 2 electrons to one nitrogen, oxygen, phosphorus or sulphur atom, or a halogen atom,
R1 represents a hydrogen atom or one or more substitutions on the phenyl group, chosen from a $(C_{1-6})$alkyl and $(C_{6-18})$ aryl radical,
Y is a counter-ion (when m=1),
m is 0 or 1,
between C and N, represented by a curved line, there is a series of atoms forming, with the carbon, nitrogen and ruthenium atoms shown in formulae (I) and (II), the metallocycle, which is formed by between 5 and 8 atoms (including the carbon, nitrogen and ruthenium atoms shown in formulae (I) and (II)).

The compounds of the invention can be in the form of salts, solvates and/or pharmaceutically acceptable prodrugs. The prodrugs are variations of the compounds of the invention which can be transformed in vivo into compounds with formula (I) or (II) according to the invention.

According to the invention, the term "alkyl" means a linear or branched hydrocarbonated radical advantageously having between 1 and 6 carbon atoms, such as methyl, ethyl, propyl, isopropyl, butyl, isobutyl, tert-butyl, pentyl, neopentyl, n-hexyl, etc. The $C_1$-$C_4$ groups are preferred. The alkyl groups can be substituted by an aryl group as defined below, in which case one talks of an arylalkyl group. Examples of arylalkyl groups are benzyl and phenethyl in particular.

The "aryl" groups are hydrocarbonated aromatic mono-, bi- or tri-cyclic systems, possibly interrupted by at least one heteroatom (in particular O, S or N). Preferably, the aryl groups include the hydrocarbonated aromatic monocyclic or bi-cyclic systems having between 6 and 18 carbon atoms, and even more preferably 6 carbon atoms. One can cite, for example, the phenyl, naphthyl and bi-phenyl groups. When they are interrupted by heteroatoms, the aryl groups include the pyridyl, imidazoyl, pyrrolyl and furanyl cycles. The aryl groups can possibly have one or more substituents, chosen in particular from a halogen atom, an alkyl group as defined above, an alkoxy (—O-alkyl), thiol, thioether (—S-alkyl), hydroxyl, nitro, cyano and ester (—$CO_2$-alkyl) radical.

"Halogen" is understood as meaning a fluorine, chlorine, bromine or iodine atom. The halogen atom is advantageously chlorine.

The donor ligands with two electrons to one nitrogen, oxygen, phosphorus or sulphur atom include, for example, $H_2O$, di($(C_{1-6})$alkyl)O, di($(C_{1-6})$alkyl)S, di($(C_{1-6})$alkyl)S(O), ($(C_{1-6})$alkyl)$SO_3^-$, di($(C_{1-6})$alkyl)C=O, $(C_{1-6})$alkyl$CO_2^-$.

Other ligands include in particular nitrile ligands, such as for example ligands with the formula $(C_{1-6})$alkylCN (in particular $CH_3CN$) and pyridine ligands, possibly substituted, on one or more carbon atoms from the pyridine cycles, by a $(C_{1-6})$alkyl radical or a halogen atom, as defined above.

Among other ligands, one can cite in particular the primary $(C_{1-6})$alkyl amines such as methylamine or ethylamine.

The donor ligands with two electrons to one phosphorus atom include ligands of the phosphine type. Advantageously, they have the formula $P(Ph)_{3-x}(alkyl)_x$, with x representing 0, 1 or 2 (preferably x represents 2) (Ph representing the phenyl group). Of these ligands, one can cite in particular $P(Ph)(CH_3)_2$.

According to one particular embodiment, in the case of formula (II), at least two of the $L_1$, $L_2$, $L_3$ and $L_4$ groups, taken two by two, can be linked by at least one covalent bond. Within this framework, one can cite in particular the bipyridine or phenanthroline motifs, possibly substituted, in particular by at least one alkyl radical as defined above. In the case of the donor ligands with two electrons to one phosphorus atom, one can advantageously cite the bidented ligands with the formula $PR'_2(alkylidene)PR'_2$, with R' representing an alkyl or aryl (preferably phenyl) group, and the alkylidene group including groups of the type $C_nH_{2n}$, or $(CR^1R^2)_n$, with n=1 to 6 (preferably 2 or 3) and R1 and R2, identical or different, representing an alkyl or aryl group as defined above, the alkylidene group corresponding to the covalent bond linking at least two of the $L_1$, $L_2$, $L_3$ and $L_4$ groups. Within this framework, one can in particular cite the bidented 1,2-bis-diphenylephosphinoethane ligand.

Therefore, preferably, the compounds of the invention have at least one $L_1$, $L_2$, $L_3$ and $L_4$ group representing a donor ligand with two electrons to one nitrogen or phosphorus atom, in particular a pyridine, phosphine (e.g. with the formula $P(Ph)_{3-x}(alkyl)_x$, as defined above), bipyridine or phenanthroline group, said groups possibly be substituted.

According to another particular embodiment of the invention, in the case of formula (II), at least two of the $L_1$, $L_2$, $L_3$ and $L_4$ groups represent nitrile ligands, such as, for example, ligands with the formula $(C_{1-6})$alkylCN (in particular $CH_3CN$).

According to another particular embodiment of the invention, in the case of formula (II), two of the $L_1$, $L_2$, $L_3$ and $L_4$ groups represent nitrile ligands, such as for example ligands with the formula $(C_{1-6})$alkylCN (in particular $CH_3CN$), and the two other ligands are linked by at least one covalent bond, advantageously such as those described above.

In the compounds according to the invention, $Y^-$ is a counter-ion and is only present in the compound when the ruthenium complex carries a positive charge. $Y^-$ is preferably a slightly nucleophilic anion, such as, for example, $BF_4^-$, $PF_6^-$, $CF_3SO_3^-$, $CF_3CO_2^-$, $CH_3CO_2^-$ and $NO_3^-$, in particular $PF_6^-$.

According to one particular embodiment of the invention, m is equal to 1.

The curved line represents with the carbon, nitrogen and ruthenium atoms shown in formulae (I) et (II), the metallocycle. This metallocycle is generally formed by between 5 and 8 atoms (including the carbon, nitrogen and ruthenium atoms shown in formulae (I) and (II)). Typically, the atoms of the metallocycle (other than those shown in formulae (I) and (II)) are chosen from carbon, nitrogen, oxygen or sulphur atoms. Each of these atoms can form, independently of the metallocycle, linear or cyclic structures, saturated or not, for which there are no particular limitations.

Therefore, of the structural units including a metallocycle with 5 or 6 atoms (including the Ru, C and N atoms shown in formulae (I) and (II)), one can cite in particular:

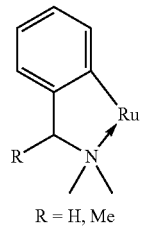

(1)

R = H, Me

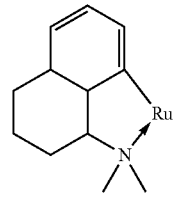

(2)

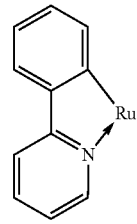

(3)

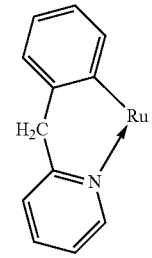

(4)

Of other structures including a metallocycle with 6 or 7 atoms, one can cite in particular:

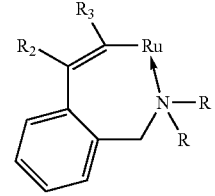

(5)

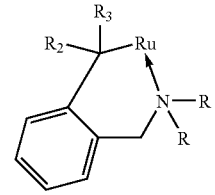

(6)

with R, identical or different, representing H or an alkyl radical, preferably methyl, and $R_2$ and $R_3$, identical or different, representing a hydrogen atom, a halogen atom, an alkyl group as defined above, an alkoxy (—O-alkyl), thiol, thioether (—S-alkyl), hydroxyl, nitro, cyano and ester (—$CO_2$-alkyl) radical.

In the metallocycle (5), $R_2$ and $R_3$ preferably both represent $CO_2Me$ and/or the two Rs represent a methyl radical.

In the metallocycle (6), $R_2$ preferably represents H and $R_3$ a methyl radical (Me) and/or the two Rs represent a methyl radical.

The present invention also concerns optical and geometric isomers, taken individually or in a mixture (in particular racemates), of the complex ruthenium compounds (II).

Advantageously, the nitrogen atom of the metallocycle and shown in formulae (I) and (II) is not a nitrogen atom included in a benzodiazepine type structure, in particular the compounds described in Organometallics, vol. 21, 2002, pp 5437-5438.

According to a particular embodiment of the invention, the compounds according to the invention are not the following compounds (described in Organometallics, vol. 21, 2002, pp 1184-1189).

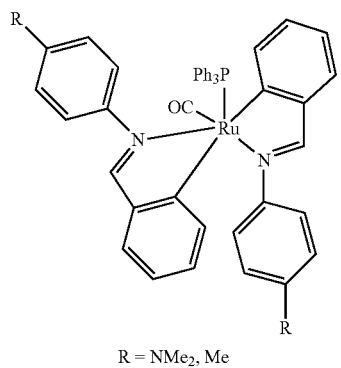

R = NMe₂, Me

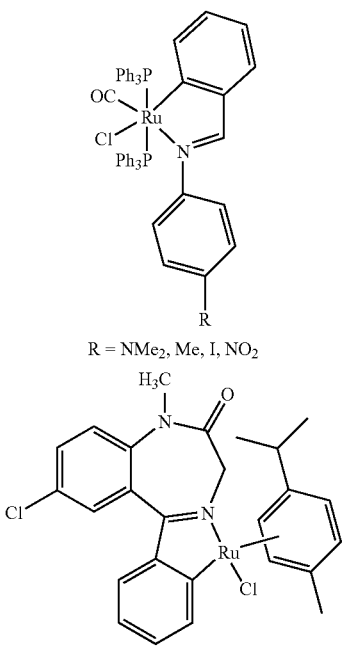

R = NMe₂, Me, I, NO₂

Of the compounds with formula (I) or (II), one can cite in particular the compounds shown in FIG. 8 (compounds numbered 3-6 and 8-29). In particular, the compounds numbered 9, 11, 12, 14-29 and, more particularly, compounds 9, 11 and 12.

Therefore, the object of the invention is also compounds 9, 11, 12 and 14-29. Preferably, compounds 9, 11, 12 and 28.

These compounds can be used as medicines, and in particular for treating illnesses linked to cell hyperproliferation, in particular cancers, as described in the present invention.

There are different synthesis methods for obtaining the compounds according to the invention. The most advantageous preparation method is the one involving the so-called the cyclometallation reaction. This reaction makes use of the particular chemical properties of the metals where this reaction is observed. Certain transition metals are in fact capable, in mild conditions, of activating a C—H bond by means of which they directly substitute the hydrogen atom in order to form the cyclometallised compound. Palladium is certainly the most widely used metal for this type of reaction. Several articles from journals (A. D. Ryabov, Chem. Rev. 1990, 90, 403-424) have been dedicated to this reaction and to the particular properties of the resulting compounds. As regards the ruthenium compounds, a method for preparing these compounds was published in Organometallics 1999, 18, 2390-2394.

Other synthesis methods are also possible, in particular when the direct C—H activation reaction by the transition metal can not be implemented. In these instances, the organic nitrogenous coordinate is metallised on the carbon by mercury(II) and the organomercurised compound thus obtained can be transmetallised on the ruthenium compound (see J. Organometal. Chem. 1995, 494, 187-193, for mercury compounds, and Inorg. Chim. Acta 1996, 249, 63-67, for the transmetallation reaction).

Therefore, the compounds of the present invention can be obtained from the A and B families of compounds as described below.

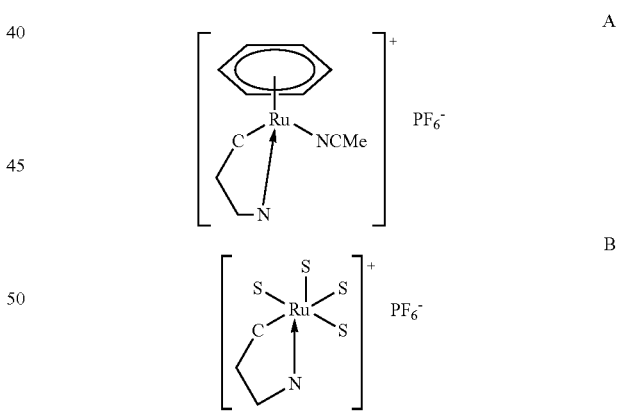

In these families of compounds, the "metallocyclic" unit represents in particular and schematically units (1) to (6) described above.

The synthesis methods for obtaining these two families of compounds (A) or (B) (respectively included in formulae (I) and (II), with S representing an $NCCH_3$ acetonitrile group) are either the so-called direct cyclometallation method by means of activating the ortho C—H bond of the aryl, or the transmetallation method by means of an organomercurised compound. The general synthesis diagram for compounds A and B is summarised in the following figure:

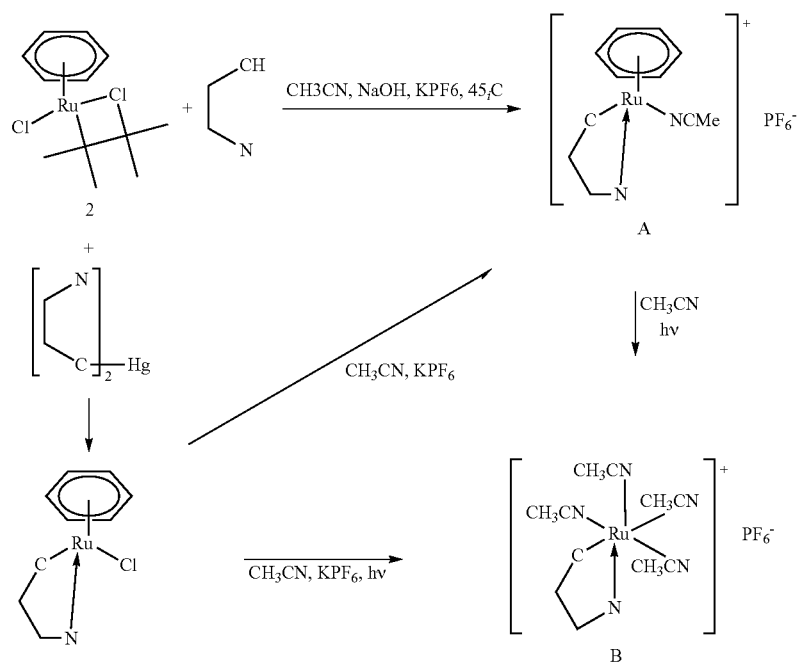

The compounds of families A and B with the different cyclometallised organic coordinates can be modified by substituting one or two acetonitrile ligands respectively by means of a monodented ligand such as a phosphine $P(Ph)_3\ x(alkyl)_x$, as defined above, which led to C and D type compounds, or by means of a bidented ligand such as bipyridine or phenanthroline or else the bidented ligand containing phosphorus, such as 1,2-bisdiphenyl phosphino ethane, which led to the type E compounds.

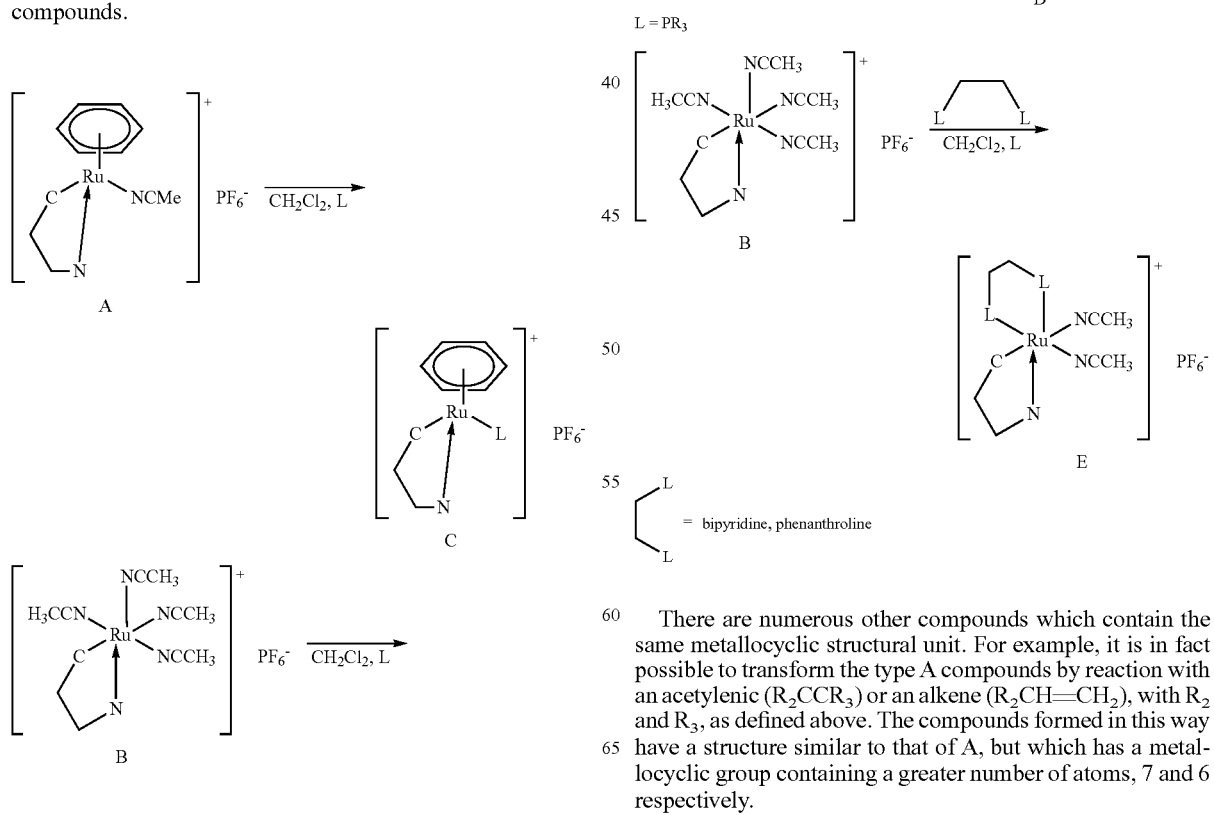

There are numerous other compounds which contain the same metallocyclic structural unit. For example, it is in fact possible to transform the type A compounds by reaction with an acetylenic ($R_2CCR_3$) or an alkene ($R_2CH\!=\!\!CH_2$), with $R_2$ and $R_3$, as defined above. The compounds formed in this way have a structure similar to that of A, but which has a metallocyclic group containing a greater number of atoms, 7 and 6 respectively.

The modified compounds are in particular the following:

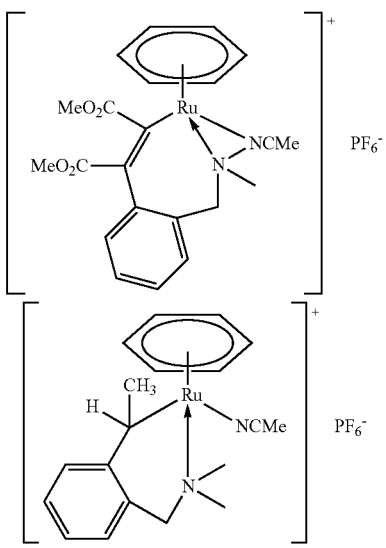

The synthesis of these two compounds is described in Bull. Soc. Chim. Fr. 1997, 134, 947-954 and in Organometallics 2003, 22, 347-354. The same reactions as those leading to compounds C, D and E can be applied to these types and thus increase the number of compounds having the same anticancerous properties.

As specified above, the compositions according to the invention are particularly advantageous for treating illnesses linked to cell hyperproliferation, in particular cancers. These cancers include those with solid or liquid tumours. The cancers correspond in particular to glioblastomas, (promyelocytary) leukemias, cancers of the prostate, the ovaries, the lungs, the breasts, the digestive tract, in particular of the liver, of the pancreas, of the head and of the neck, of the colon, of the bladder, non-Hodgkin lymphomas and melanomas.

The object of the present invention is also the use of at least one compound with formula (I) or (II), as defined above, within the framework of the preparation of a pharmaceutical composition for treating illnesses linked to cell hyperproliferation, in particular cancers.

The compounds according to the invention have an antiproliferative effect with respect to tumoral cells. They are particularly useful for treating cancers by accumulating the tumoral cells in the G0/G1 phase, and possibly by inducing apoptosis in tumoral cells.

In fact, without wishing to be associated with any theory of the invention, the compounds according to the invention seem in particular capable of accumulating the tumoral cells in the G0/G1 phase, and so by blocking their cell cycle, but also seem capable of generating their apoptosis rapidly, in particular when their concentration is increased—a sign of a dose-dependent toxicity.

Furthermore, the compounds according to the invention are particularly advantageous for treating tumours which are resistant to cisplatinum or to other anticancer drugs.

The compounds or compositions according to the invention can be administered in different ways and in different forms. Therefore, they can be administered systemically, orally, by inhalation or by injection, for example intravenously, intra-muscularly, subcutaneously, transdermically, intraarterially, etc., the intravenous, intramuscular, subcutaneous, oral and inhalation methods being preferred. For the injections, the compounds are generally conditioned in the form of liquid suspensions, which can be injected by means of syringes or perfusions, for example. With regard to this, the compounds are generally dissolved in saline, physiological, isotonic, buffered etc. solutions, compatible with pharmaceutical use and known to the person skilled in the art. Therefore, the compositions can contain one or more agents or vehicles chosen from dispersants, solubilisers, stabilisers, preservatives, etc. Agents or vehicles which can be used in liquid and/or injectable formulations are in particular methylcellulose, hydroxymethylcellulose, carboxymethylcellulose, polysorbate 80, mannitol, gelatin, lactose, vegetable oils, acacia, etc.

The compounds can also be administered in the form of gels, oils, tablets, suppositories, powders, capsules, aerosols, etc., possibly by means of galenic forms or devices guaranteeing prolonged and/or delayed release. For this type of formulation, it is advantageous to use an agent such as cellulose, carbonates or starches.

It goes without saying that the throughput and/or the dose injected can be adapted by the person skilled in the art dependently upon the patient, the pathology in question, the administration method, etc. Typically, the compounds are administered at doses which can vary between 0.1 µg and 100 mg/kg body weight, and more generally between 0.01 and 10 mg/kg, typically between 0.1 and 10 mg/kg. Furthermore, repeated injections can be given, should the occasion arise. On the other hand, for chronic treatments, delay or prolongation systems can be advantageous.

The invention also concerns a method for treating a pathology linked to cell hyperproliferation, in particular a cancer, by administering to a subject suffering from this type of pathology an effective quantity of one of the compounds according to the invention.

Within the context of the invention, the term "treatment" means the preventive, curative, palliative treatment as well as patient care (reduction of suffering, improvement of life span, slowing down the progression of the illness, reducing the tumoral growth, etc.). Furthermore, the treatment can be implemented in combination with other agents or chemical or physical treatments (chemotherapy, radiotherapy, gene therapy, etc.). The treatments and drugs of the invention are particularly intended for humans.

Therefore, the compounds according to the invention can advantageously be used in combination with an anti-cancer treatment implementing radiation, such as radiotherapy and brachytherapy. The radiation applied involves in particular X rays, gamma rays, ionising particles such as electrons, neutrons or carbon ions.

According to another aspect of the invention, the compounds according to the invention can be used with other chemical agents or therapeutic anti-cancer treatments, such as the following therapeutic chemical agents: cisplatinum, carboplatinum, NCS (Neocarzinostatin), Taxotere or Taxol, advantageously NCS or Taxol. The compounds according to the invention are preferably conditioned and administered in combination, separately or sequentially in relation to other agents or therapeutic treatments.

It also concerns a method for inhibiting in vivo, in vitro or ex vivo the proliferation of tumoral cells including placing said tumoral cells in contact with one of the products according to the invention. The tumoral cells can in particular originate from the pathologies specified above.

KEY TO THE FIGURES

In the following figures and examples, the terms "CDR" or as an equivalent "RDC" mean a "compound derived from ruthenium".

Figure 1:
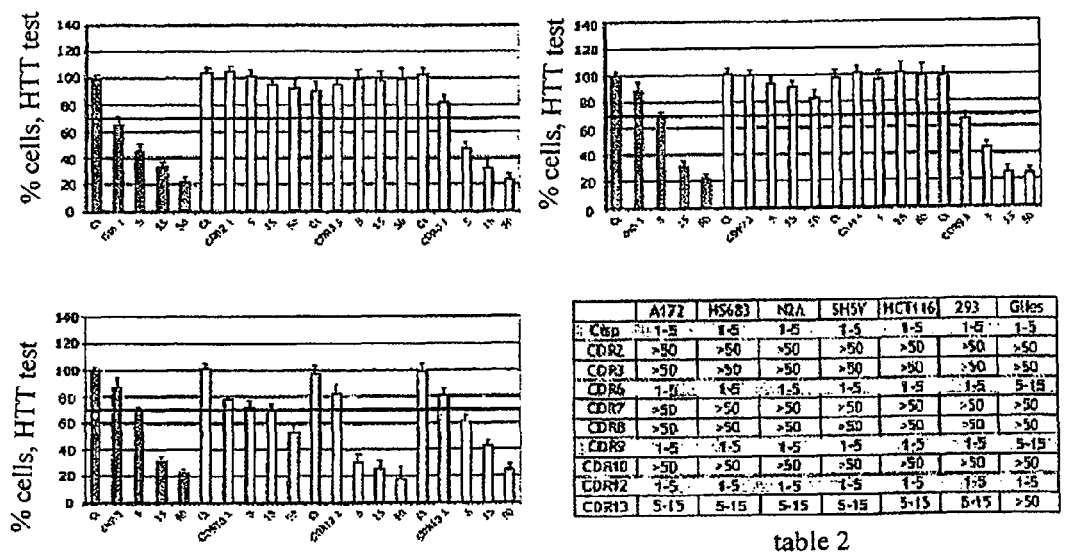

FIG. 1: The A172 cells were cultivated on plates with 96 wells in DMEM medium with 10% calf serum. At 30% confluence, the cells were treated for 48 hrs with cisplatinum or the various compounds derived from ruthenium in the concentrations indicated (1, 5, 15, 50 µM). The quantity of cells present in the wells was evaluated by an MTT (MTT, Sigma) test of which the products of the reaction are quantified with an Elisa plate reader (Metertech, USA) (490-650 nm). The results obtained were related to the values of the control condition (100% viability). The graphs show an average of 8 points with the typical spacings over one experiment representative of 4 carried out. The thick black line indicates the IC50 for each graph.

TABLE 2: a summary of the results obtained on various cell lines and primary glial cultures. The experiments were carried out under the same conditions as those described for the A172 cells. Each IC50 is an indicative value obtained over 4 independent experiments.

Figure 2:
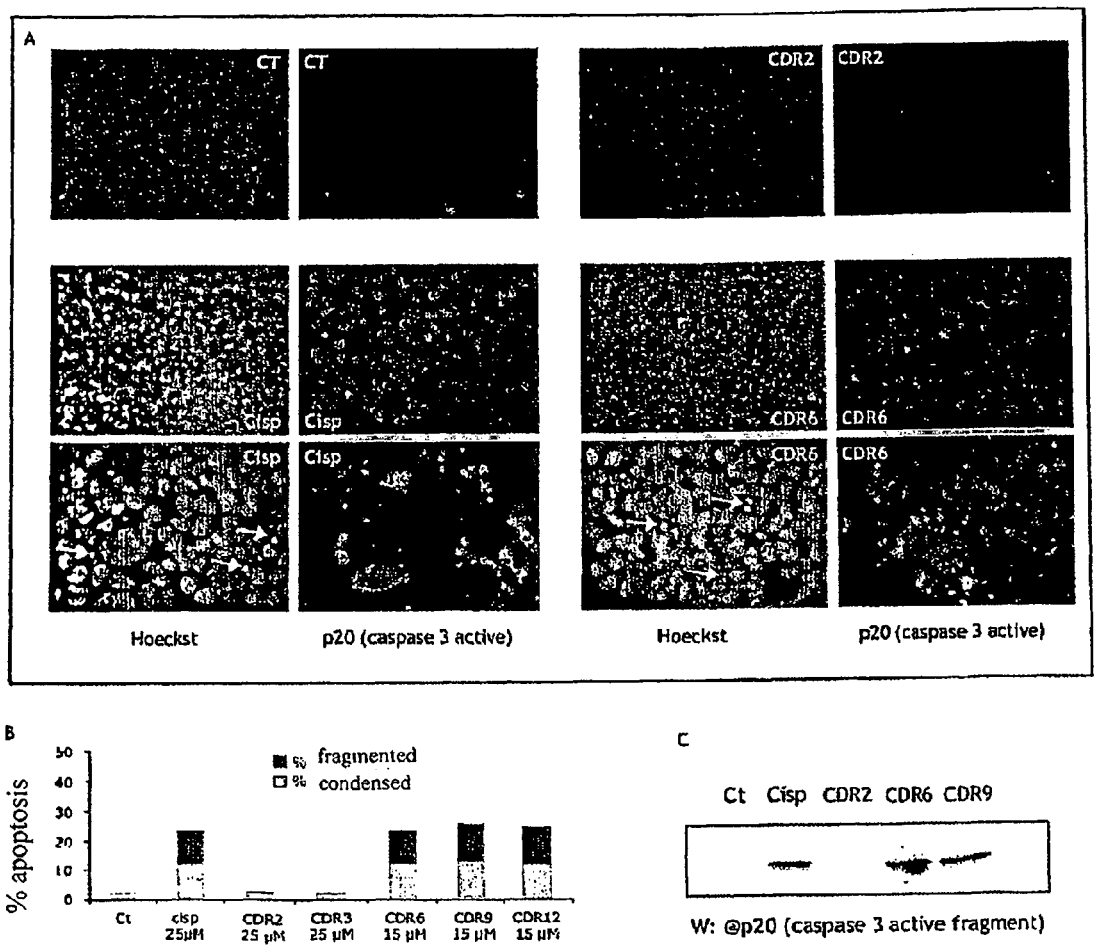

FIG. 2: A—The A172 cells were cultivated on glass slides. At 50% confluence, the cells were treated for 24 hrs with cisplatinum, CDR2 (25 µM) or CDR6 (15 µM). The cells were then fixed in 4% paraformaldehyde, permeabilised with 0.1% NP40 and marked with Hoechst dye (blue) and the anti-p20 antibody (active fragment of caspase 3, in red). The cells were then observed under the fluorescence microscope. B—Graphic representation of the number of cells with an apoptotic, fragmented or condensed nucleus. The bars are an average of two slides from one experiment representative of 3 carried out. C—In parallel, proteic extracts were prepared from cells treated with various drugs (cisplatinum 15 µM; CDR225 µM; CDR615 µM; CDR915 µM) and following denaturation the extracts were deposited on a !0% SDS-Page gel. After migration, the proteins were transferred onto nitrocellulose (Biorad, 0.2 µm) and the p20 fragment of the caspase 3 was detected by Western blot with an anti-p20 antibody (1/1000, R&D System).

Figure 3:
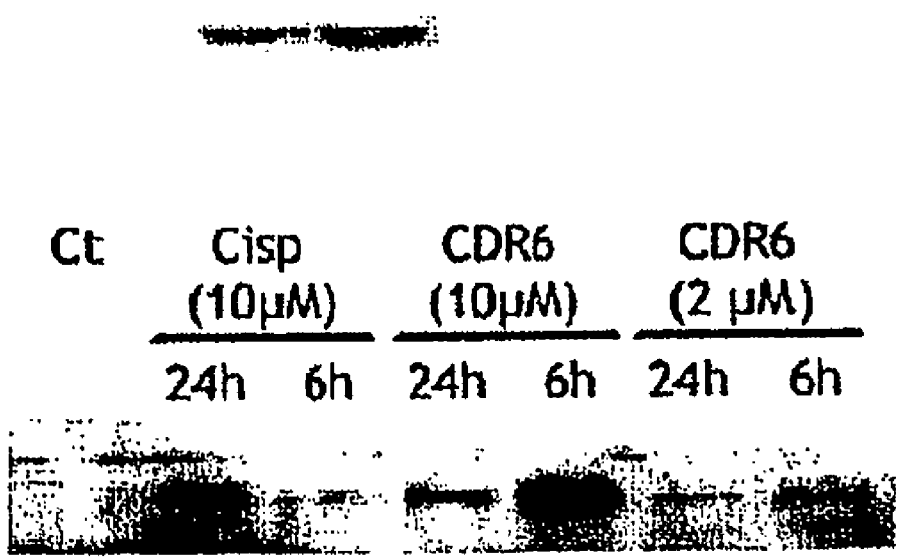
Figure 3:
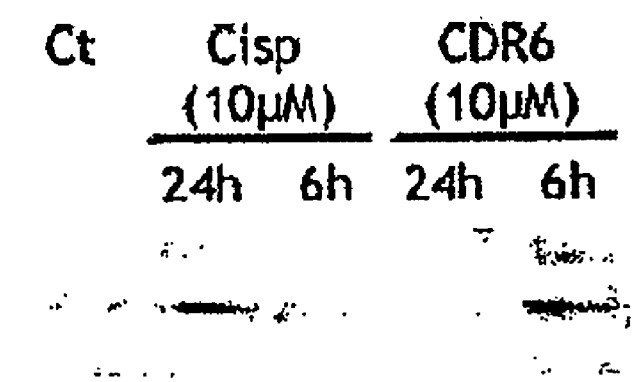

FIG. 3: Detection of p53 and p73 in A172 cells treated with CDR. The A172 cells were treated with the concentrations indicated (2, 5 or 10 µM) with the various compounds and for the periods of time indicated (24 hrs or 6 hrs). The proteins were extracted with a lysis buffer and were separated on 10% SDS-Page gel. After being transferred onto nitrocellulose, the p53 and p73 proteins were detected by Western blot using anti-p53 (pAb1801) and anti-p73 (1/200, Ab2, Oncogene) antibody.

Figure 4:
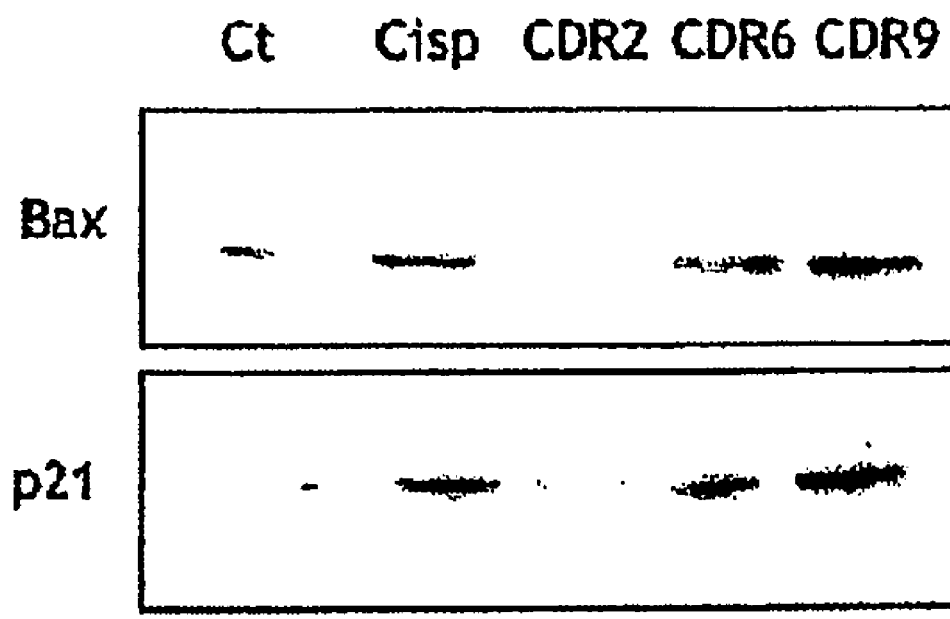

FIG. 4: Detection of p21 and Bax in A172 cells treated with CDR. The A172 cells were treated with the various compounds (10 µM) for 24 hrs. The proteins were extracted with a lysis buffer and were separated on 10% SDS-Page gel. After being transferred onto nitrocellulose, the p21 and Bax proteins were detected by Western blot using anti-p21 (1/200, Oncogene) and anti-Bax (1/2000, Santacruz) antibody.

Figure 5:
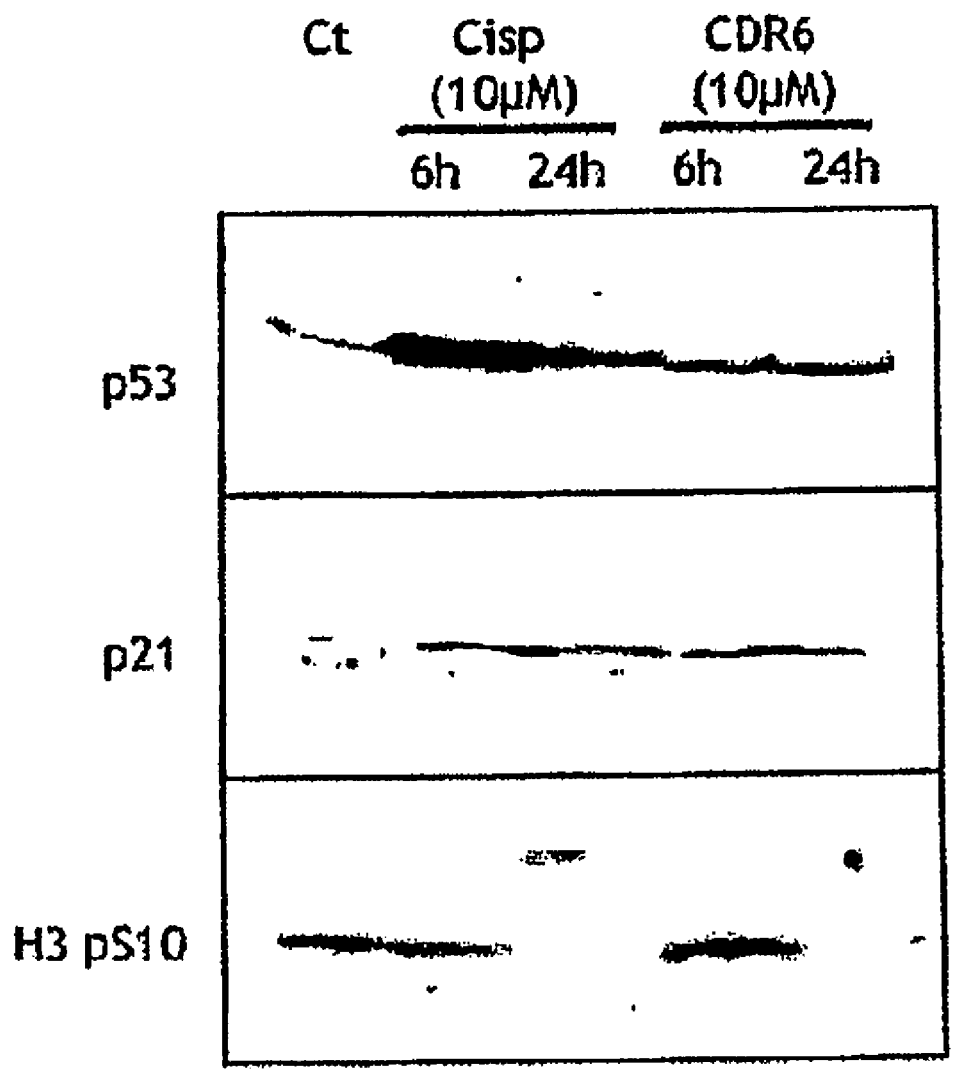

FIG. 5: Detection of p53, p21 and of the phosphorylation of histone H3 in the HCT116 cells treated with CDR. The HCT116 cells were treated with the various compounds (10 µM) and for the periods of time indicated (24 hrs or 6 hrs). The proteins were extracted with a lysis buffer and were separated on 10% SDS-Page gel. After being transferred onto nitrocellulose, the p53, p21 proteins and histone H3 were detected by Western blot using anti-p53 (pAb1801), anti-p21 (1/200, Oncogene) antibody and anti-phospho serine 10 of histone H3 (1/2000, Santacruz).

Figure 6:
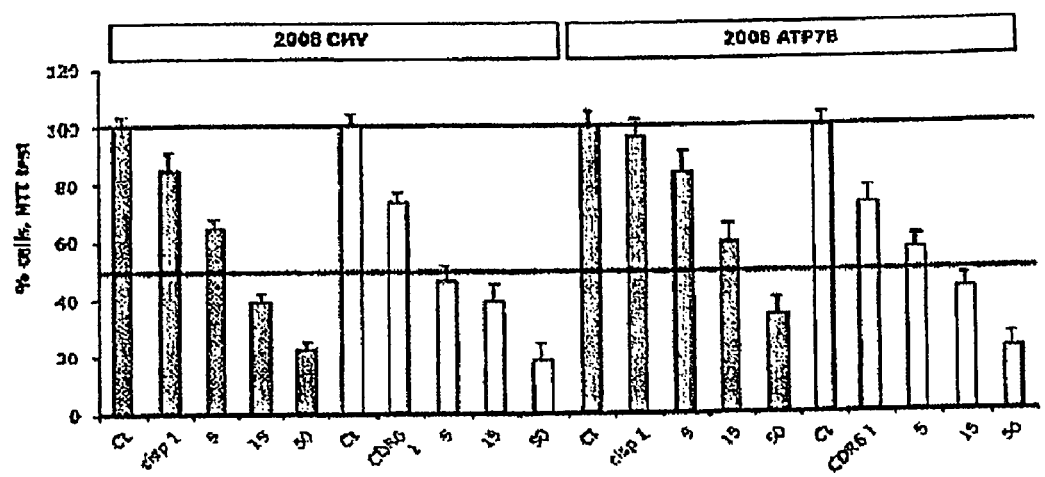

FIG. 6: The 2008/CMV and 2008/ATP7B cells (contributed by Dr. Howell) were cultivated in plates with 96 wells in DMEM medium with 10% calf serum. At 30% confluence, the cells were treated for 48 hrs with cisplatinum or the various compounds derived from ruthenium in the concentrations indicated (1, 5, 15, 50 µM). The quantity of cells present in the wells was evaluated by an MTT (MTT, Sigma) test. The results obtained were related to the values of the control condition (100% viability). The graphs show an average of 8 points with the typical spacings over one experiment representative of 3 carried out. The thick black line indicates the IC50 for each graph.

Figure 7:
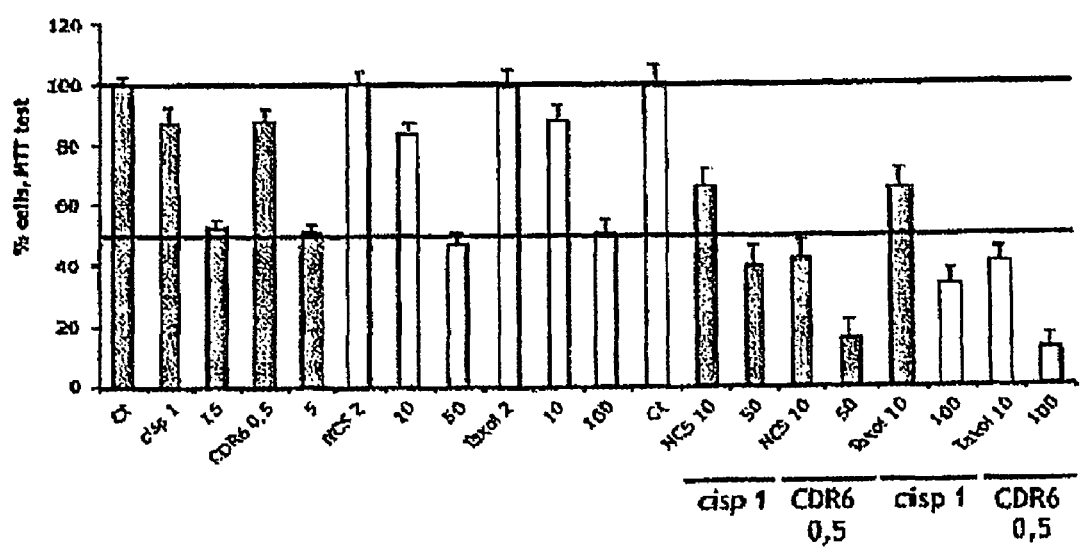

FIG. 7: The A172 cells were cultivated in plates with 96 wells in DMEM medium with 10% calf serum. At 30% confluence, the cells were treated for 48 hrs with cisplatinum, CDR6, NCS (Neocarzinostatin), Taxol or a combination of these drugs in the concentrations indicated. The quantity of cells present in the wells was evaluated by an MTT (MTT, Sigma) test, the reaction products of which are quantified with an Elisa plate reader (Metertech, USA) (490-650 nm). The results obtained were related to the control condition values (100% viability). The graphs show an average of 8 points with the typical spacings over one experiment representative of 4 carried out. The thick black line indicates the IC50 for each graph.

FIG. 8: Examples of compounds with formula (I) or (II), with the exception of the compounds numbered 1 and 2 which are shown as references.

Figure 9:
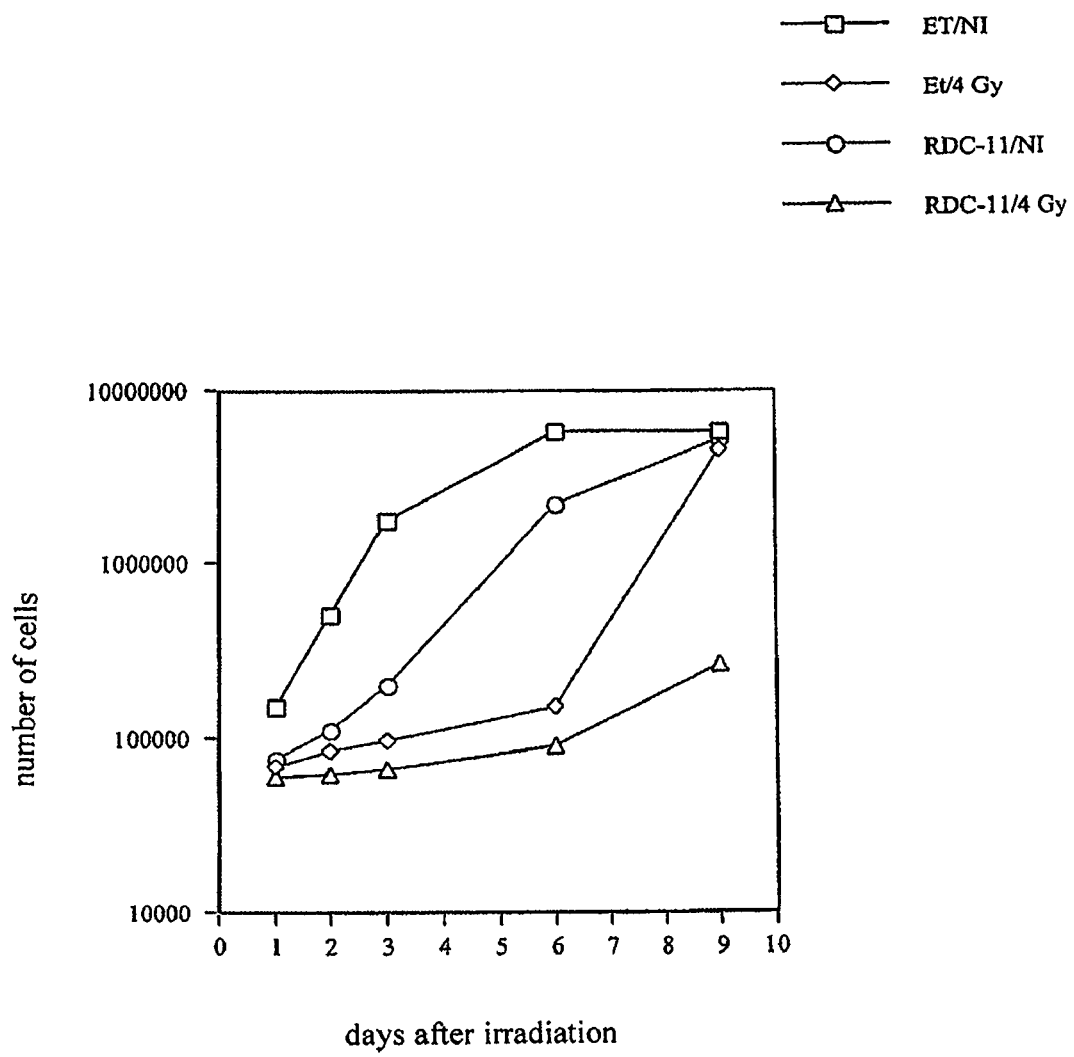

FIG. 9: Effect of irradiation (4 Gy), of treatment using RDC-11 (RDC-11/NI) and of the "irradiation+RDC-11" (RDC-11/4 Gy) association upon the proliferation of RDM4 cells in culture.

Figure 10:
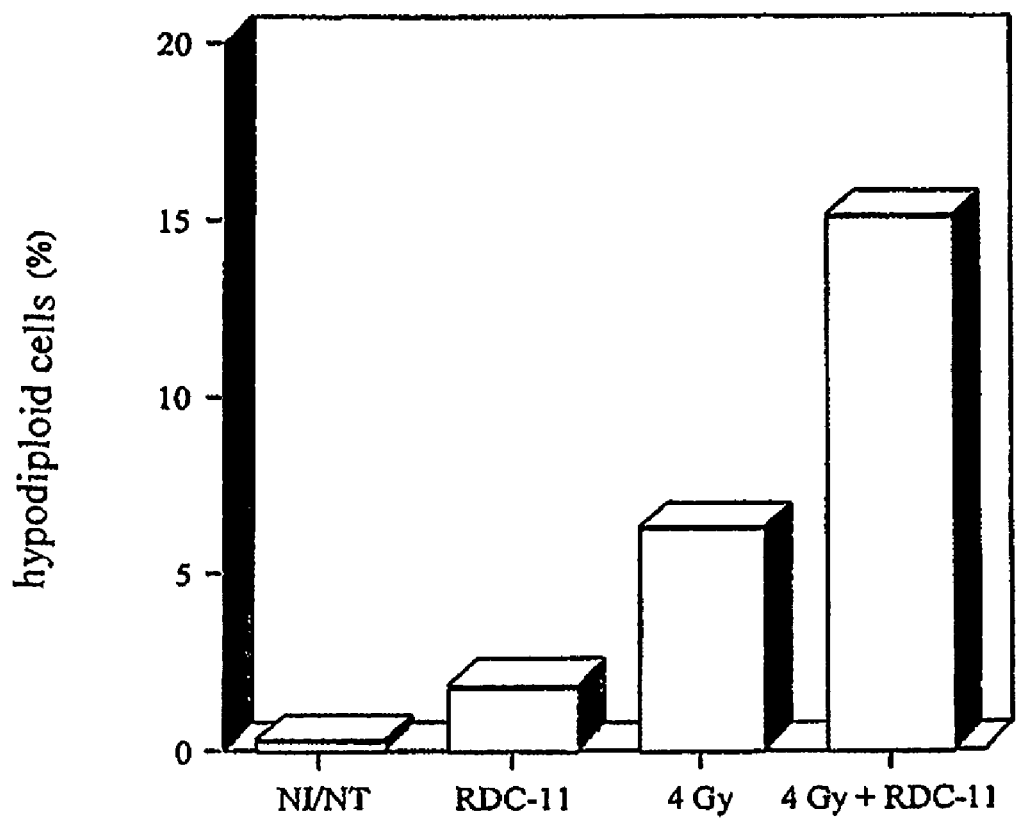

FIG. 10: The percentage of apoptosis on RDM4 cells induced by RDC-11 (RDC-11), by irradiation by rapid neutrons (4 Gy), or by the combination of the two treatments (4 Gy+RDC-11), three days after the start of the treatment. The analysis was implemented by flux cytometry, after marking the cells with propidium iodure.

Figure 11:
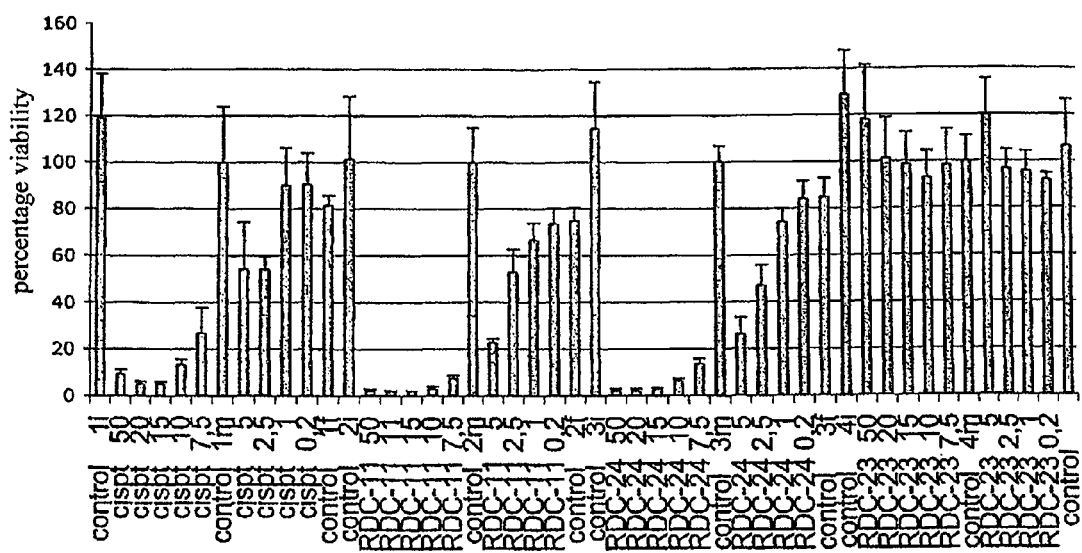

FIG. 11: The percentage viability of HCT-116 cells in the presence of RDC-11, RDC-24 and RDC-23 or Cisplatinum in different concentrations.

Figure 12:
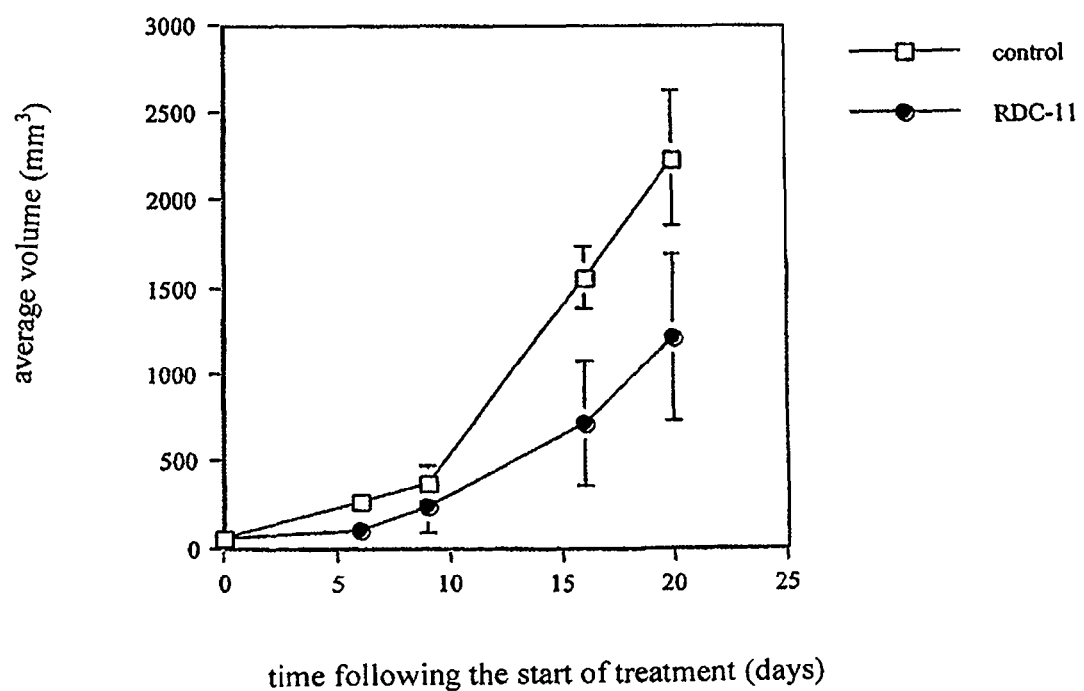

FIG. 12: Average volume ($mm^3$) of apparent tumours of U-87 cells (human glioblastoma) grafted onto athymic nude/nude SWISS mice as a function of time (days) following the start of treatment with RDC-11 or D-PBS (control).

Figure 13:
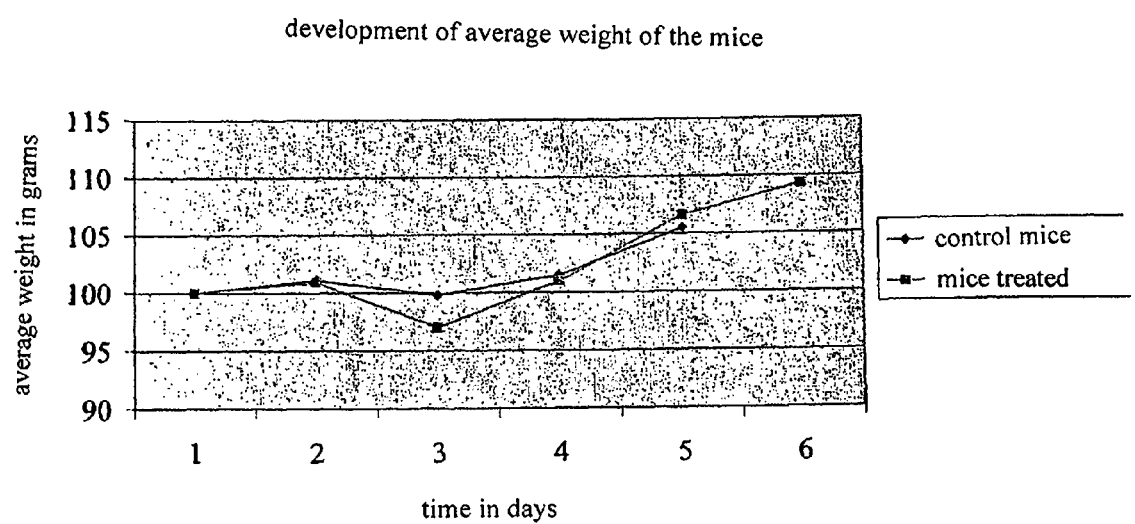

FIG. 13: Development of the average weight of SWISS mice grafted with U-87 cells (human glioblastoma) as a function of time (days) following the start of treatment with RDC-11 or D-PBS (control).

Figure 14:
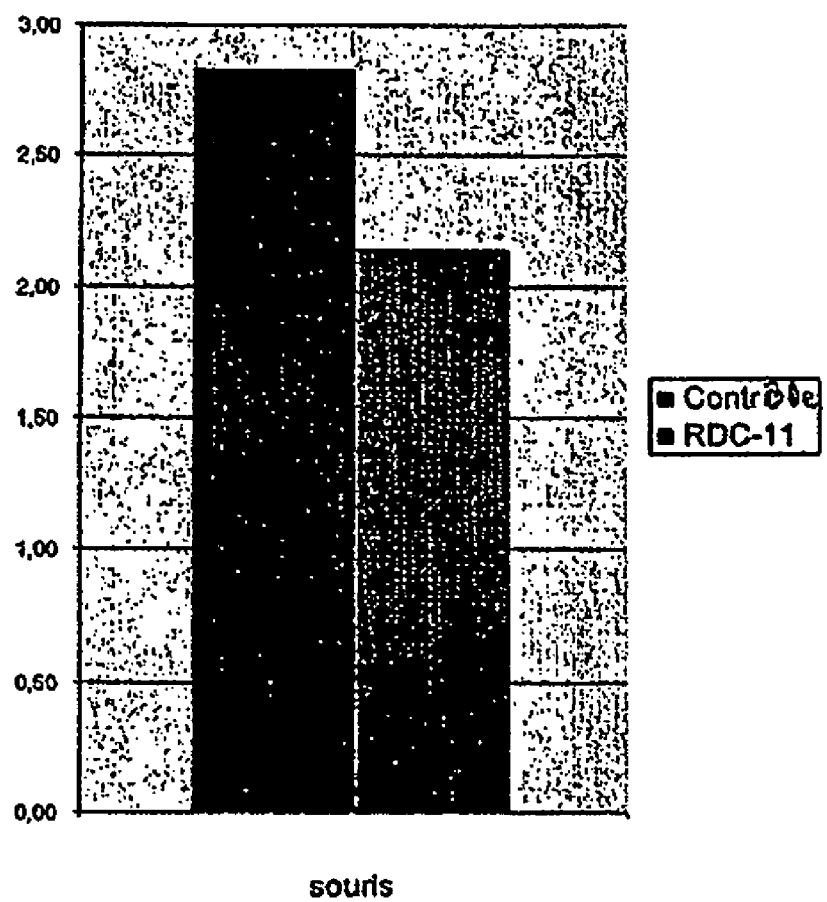

FIG. 14: Weight of the tumours (after dissection) of SWISS mice grafted with U-87 cells (human glioblastoma) following treatment with RDC-11 or D-PBS (control).

Other aspects and advantages of the current application will become clear from reading the following examples which must be considered as illustrative and not restrictive.

EXAMPLES

1—Methods for Synthesising Compounds According to the Invention

The cyclometallised ruthenium compounds (II) are sensitive to oxygen in the air and to acids. Consequently, all of the solvents must be perfectly dried and de-oxygenated before being used. The manipulations take place in a controlled atmosphere (nitrogen or argon) using the Schlenk tube technique.

Synthesis of Compound 5 (According to Organometallics, 1999, 18, 2390):

N,N dimethylaminomethylbenzene (0.120 mL, 0.8 mmol), NaOH (0.031 g, 0.8 mmol) and KPF6 (0.292 g, 1.6 mmol) are added to a suspension of $[(\eta^6 C_6H_6)RuCl_2]_2$ (0.2 g, 0.4 mmol) in acetonitrile (5 mL) at 20° C. for 3 days. The yellow solution obtained in this way is then filtered (chromatographed) on standardised alumina (12×3 cm) with acetonitrile as an eluent. The yellow fraction, which is dried in a vacuum, is collected. The residue obtained is re-dissolved in a minimum of acetonitrile (2 mL). The addition of ethylic ether to this solution brings about the crystallisation of a bright yellow product which is the expected compound (yield 0.32 g, 80%).

Synthesis of Compound 6

$[Ru(\eta^6-C_6H_6)-2-(CH_2NMe_2)-C_6H_4-(PMe_2Ph)]PF_6$: $PMe_2Ph$ (0.019 mL, 0.162 mmol) is added to a yellow solution of complex 5 (0.08 g, 0.156 mmol) in $CH_2Cl_2$ (10 mL), and the resulting solution is stirred at ambient temperature for 3 hours. The solvent is evaporated in a vacuum, and the resulting residue is dissolved in a minimum of $CH_2Cl_2$ (1 mL). The addition of n-hexane brings about the precipitation of complex 6 (yield: 0.09 g, 95%). Elementary analysis. Calculated for $C_{23}H_{23}NF_6P_2Ru+½ CH_2Cl_2$: C, 44.13; H, 4.69; N, 2.19. Found: C, 44.30, H, 4.59; N, 2.16.

RMN $^1H(CD_3CN)$: 7.75 (dt, 1H, H6, $^3J=7.5$), 7.39 (tdd, 1H, p, $^3J=7.5$, $^4J=1.7$), 7.22 (td, 2H, m, $^3J=8.0$, $^4J=2.0$), 7.08 (tdd, 1H, H4 or H5, $^3J=7.1$), 7.00-6.88 (m, 3H, o and H4 or H5), 6.72 (d, 1H, H3, $^3J=7.5$), 5.74 (d, 6H, $C_6H_6$, $^3J_{HP}=1.1$), 2.85 and 2.43 ((AB, 2H, $^2J=14.5$), 2.77 (d, 3H, NMe, $^4J_{HP}=1.1$), 2.66 (s, 3H, NMe), 1.99 (d, 3H, PMe, $^2J=9.3$), 1.50 (d, 3H, PMe, $^2J=9.7$).

RMN $^{31}P$ ($CD_3CN$): 6.37 (s, 1P, $PMe_2$), -142.97 (sept, 1P, $PF_6$, $^1J=711$).

Synthesis of Compound 8 (According to Organometallics, 1999, 18, 2390):

2-phenylpyridine (6.02 mmol), NaOH (0.48 g, 6.02 mmol) and $KPF_6$ (2.22 g, 12.04 mmol) are added to a suspension of $[(eta^6-C_6H_6)RuCl_2]_2$ (1.5 g, 3.01 mmol) in acetonitrile (50 mL) at 45° C. for 20 hrs. The solvent is then evaporated in a vacuum, and the residue obtained is chromatographed on a standardised alumina column with acetonitrile as an eluent. The yellow strip is collected and dried in a vacuum. This residue is dissolved in a mixture of acetonitrile and dichloromethane (1:1); the slow diffusion of ethylic ether in this solution makes it possible to obtain compound 8 in the form of bright yellow crystals (yield 68%).

Synthesis of Compound 9

$[Ru (C_6H_4-2-C_5H_4N) (PMe_2Ph) (NCMe)_3]PF_6$ 9: $PMe_2Ph$ (0.031 mL, 0.22 mmol) is added to a yellow solution of complex 8 (0.124 g, 0.22 mmol) in $CH_3CN$ (5 mL), and the resulting solution is stirred at ambient temperature for 18 hours. The yellow/green solution is filtered on alumina with acetonitrile as an eluent. The yellow fraction is harvested and concentrated in a vacuum. The powder obtained is dissolved in a minimum of acetonitrile and ethylic ether. (1:1). The addition of n-hexane brings about the precipitation of compound 9 in the form of a yellow powder (yield: 0.122 g, 84%). Elementary analysis: Calculated for $C_{25}H_{28}N_4F_6P_2Ru$: C, 45.39, H, 4.27; N, 8.47. found: C, 45.35, H, 4.49; N, 8.33.

$RMN^1H(CD_3CN)$: 8.39 (ddd, 1H, H12, $^3J=5.8$, $^4J=1.6$, $^5J=0.8$), 8.08 (dddd, 1H, H6, $^3J=7.1$, $^4J_{HP}=4.7$, $^4J=1.3$, $^5J=0.5$), 7.89 (d, 1H, H9, $^3J=8.1$), 7.80 (d, 1H, H3, $^3J=7.8$), 7.71-7.63 (m, 3H, H10 and o), 7.53-7.49 (m, 2H, m), 7.44 (t, 1H, p, $^3J=7.4$), 7.20 (td, 1H, H5, $^3J=7.3$, $^4J=1.4$), 7.06 (td, 1H, H4, $^3J=7.5$, $^4J=1.4$), 6.92 (ddd, 1H, H11, $^3J=7.3$, $^3J=5.8$, $^4J=1.5$), 2.33 (d, 3H, NCMe, $^5J_{HP}=1.7$), 1.97 (d, 3H, NCMe, $^5J_{HP}=1.8$), 1.86 (d, 6H, $PMe_2$, $^2J_{HP}=5.8$).

RMN $^{13}C\{^1H\}$ ($CD_3CN$): 185.5 (C1), 170.2 (C8), 156.6 (C12), 147.1 (C2), 138.0 (C6), 137.5 (C10), 131.0 (Co), 129.7 (Cm), 129.3 and 129.2 (C5 and Cp), 124.4 (C4 and Cipso), 123.6 (NCMe), 122.9 (C4), 122.3 (C11), 119.4 (C9), 13.55 and 13.41 ($PMe_2$), 4.31 and 3.99 (NCMe).

RMN $^{31}P$ ($CD_3CN$): -7.08 (s, 1P, $PMe_2$), -144.40 (sept, 1P, $PF_6$, $^1J=704.6$).

Synthesis of Compound 11

$[Ru(C_6H_4-2-C_5H_4N)(phen)(NCMe)_2]PF_6$ 11: phenanthroline (0.032 g, 0.178 mmol) is added to compound 8 (0.1 g, 0.178 mmol) dissolved in $CH_2Cl_2$ (13 mL). The solution is stirred at ambient temp. for 2 days, the reaction development being followed by proton NMR. The solvent is then evaporated in a vacuum and the residue is dissolved in the minimum of acetonitrile/$CH_2Cl_2$ (1:1) and n-hexane (20 mL) and this solution is left to rest for 3 days. Product 11 is obtained in the form of dark brown crystals (yield: 0.099 g, 84%). Elementary analysis: calculated for $C_{27}H_{22}N_5F_6PRu$: C, 48.95, H, 3.35; N, 10.57. found: C, 48.00, H, 3.58; N, 10.60.

RMN $^1H(CD_3CN)$: 9.72 (dd, 1H, H14, $^3J=5.0$, $^4J=1.5$), 8.72 (dd, 1H, H16, $^3J=8.2$, $^4J=1.4$), 8.30 (dd, 1H, H23, $^3J=7.4$, $^4J=1.3$), 8.22 (m, 1H, H18), 8.20-8.17 (m, 2H, H15 and H11), 8.15 (dd, 1H, H12, $^3J=5.3$, $^4J=1.4$), 8.03 (d, 1H, H19, $^3J=8.9$), 7.88 (dd, 1H, H9, $^3J=7.8$, $^4J=1.2$), 7.84 (d, 1H, H6, $^3J=8.1$), 7.48 (ddd, 1H, H5, $^3J=8.1$, $^3J=7.4$, $^4J=1.6$), 7.37 (dd, 1H, H10, $^3J=8.1$, $^3J=5.4$), 7.34 (ddd, 1H, H3, $^3J=5.7$, $^4J=1.6$, $^5J=0.8$), 7.30 (dd, 1H, H21, $^3J=7.3$, $^4J=1.3$), 7.11 (dd, 1H, H22, $^3J=7.7$, $^3J=7.2$), 6.58 (ddd, 1H, H4, $^3J=7.3$, $^3J=5.8$, $^4J=1.5$), 2.29 (s, 3H, NCMe), 2.07 (s, 3H, NCMe).

RMN $^{13}C\{^1H\}$ ($CD_3CN$): 192.6 (C1), 169.5 (C8), 156.1 (C15), 152.0 (C3), 151.5 (C14), 150.7 (C2), 147.4 and 146.8 (C26 and C25), 139.0 (C23), 136.5 (C16), 136.4 (C5), 135 (C18), 131.3 and 131.1 (C20 and C17), 129.2 (C21), 128.4 (C12), 128.3 (C19), 126.8 (C11), 125.1 (C10), 124.7 (C9), 125.5 and 122.7(NCMe), 121.9 (C4), 121.5 (C22), 118.8 (C6), 4.40 and 4.01 (NCMe).

Synthesis of Compound 12:

$[Ru(C_6H_4-2-C_5H_4N)(4,4'-dimethyl-2,2'-bipyridine)(NCMe)_2]PF_6$ 12: 4,4'-diMe-2,2'-bipyridine (0.032 g, 0.181 mmol) is added to compound 8 (0.102 g, 0.181 mmol) dissolved in $CH_2Cl_2$ (13 mL). The solution is stirred at ambient temperature for 2 days, the reaction development being followed by proton NMR. The solvent is then evaporated in a vacuum, and the residue is dissolved in the minimum of acetonitrile/$Et_2O$ (1:1) and n-hexane (30 mL), and this solution is left to rest for 3 days. Product 11 is obtained in the form of dark brown crystals Anal. Calcd. for $C_{27}H_{26}N_5F_6PRu$ C, 48.65, H, 3.93; N, 10.51. found: C, 48.83, H, 4.32; N, 10.30.

RMN $^1H(CD_3CN)$: 9.18 (d, 1H, H14, $^3J=5.5$), 8.30 (s, 1H, H16), 8.21 (ddd, 1H, H6, $^3J=7.4$, $^4J=1.3$, $^5J=0.5$), 8.09 (s, 1H, H17), 7.85-7.81 (m, 2H, H9 and H12), 7.68-7.66 (m, 2H, H15 and H19), 7.52 (ddd, 1H, H10, $^3J=8.2$, $^3J=7.4$, $^4J=1.6$), 7.44 (ddd, 1H, H3, $^3J=5.7$, $^4J=1.6$, $^5J=0.8$), 7.24 (td, 1H, H11, $^3J=7.3$, $^4J=1.3$), 7.05 (ddd, 1H, H5, $^3J=7.7$, $^3J=7.2$, $^4J=1.3$), 6.85 (dd, 1H, H18, $^3J=5.9$, $^4J=1.8$), 6.73 (ddd, 1H, H4, $^3J=7.3$, $^3J=5.7$, $^4J=1.5$), 2.64 and 2.34 (2s, 6H, $CH_3$), 2.21 and 2.19 (2s, 6H, NCMe).

Synthesis of Compound 13

$[Ru-2-(CH_2NMe_2)-C_6H_4-(bipy)(NCMe)_2]PF_6$

An equivalent of 2,2'-bipyridine is added to a solution of 5 (0.1 g) in 15 mL acetonitrile. The mixture is stirred for 24 hrs. The purple solution obtained is evaporated in a vacuum, and the residue is chromatographed on an alumina column with acetonitrile as an eluent. The dark purple strip is collected and evaporated in a vacuum. Compound 13 is obtained in the form of dark purple crystals by diffusing ethylic ether in a solution of 13 dissolved in the minimum of dichloromethane/acetonitrile (1:1) (yield: 53%). Elementary analysis: Calculated. for $C_{29}H_{38}N_5F_6PRu$: C, 49.57, H, 5.45; N, 9.97. found: C, 49.21, H, 5.60; N, 9.62.

RMN $^1$H (CD$_3$CN): 9.52 (dd, 1H, $^3$J 6.0, $^4$J 1.6, H2"), 8.69 (dd, 1H, $^3$J 5.5, $^4$J 1.1, H2'), 8.65 (d, 1H, $^3$J 8.2, H'''), 8.53 (d, 1H, $^3$J 7.7, H5'), 8.17 (td, 1H, $^3$J 7.7, $^4$J 1.1, H4"), 7.92 (td, 1H, $^3$J 8.2, $^4$J 1.6, H4'), 7.86-7.80 (m, 2H, H3"+H5), 7.36 (ddd, 1H, $^3$J 7.1, $^3$J 6.0, $^4$J 1.6, H3'), 7.08 (td, 1H, $^3$J 7.1, $^4$J 1.1, H4), 7.00 (d, 1H, $^3$J 7.2, H2), 6.85 (td, 1H, $^3$J 7.1, $^4$J 1.1, H3), 3.88 (d, 1H, $^2$J 13.8, CH$_2$), 3.30 (d, 1H, $^2$J 13.8, CH$_2$), 2.45 (s, 3H, NCMe), 2.18 (s, 3H, NMe$_2$), 2.07 (s, 3H, NCMe), 1.36 (s, 3H, NMe$_2$).

RMN $^{13}$C (CD$_3$CN): 168.46, 159.49, 155.80, 153.17 (C2'), 150.65 (C2"), 148.03, 137.61 (C5), 135.96 (C4"), 134.96 (C4'), 126.52 (C3"), 125.43 (C3'), 125.28 (C4), 122.82 (C5'), 122.60 (C5"), 120.76 (C2), 120.27 (C3), 118.03, 73.02 (CH$_2$), 52.00 (NMe$_2$), 50.46 (NMe$_2$), 4.00 (NCMe), 3.16 (NCMe).

Synthesis of Compounds 14 to 25:

Compounds 14 to 25 were obtained by a method similar to that used for the synthesis of 13. First of all the compounds similar to compound 5 were obtained by using, instead of N,N dimethylaminomethylbenzene, the corresponding substituted ligand. Secondly, these compounds were treated with 2,2'-bipyridine as in the example above, the yields being similar to those obtained for 13.

Synthesis of Compound 26

First of all the compound $[(\eta^6\text{-}C_6H_6)Ru(C_6H_4\text{-}2\text{-}CHCH_3NMe_2)(NCMe)]PF_6$ is synthesised using a method similar to that used in order to synthesise compound 5. In this protocol, N,N dimethylaminomethylbenzene is substituted by (R) (1,1-phenylethyldimethylamine) (0.8 mmol) and one operates in exactly the same way as for the synthesis of 5, the yields being the same. 2,2'-bipyridine (0.030 g, 0.19 mmol) is then added to a solution of $[(\eta^6\text{-}C_6H_6)Ru(C_6H_4\text{-}2\text{-}CHCH_3NMe_2)(NCMe)]PF_6$ in 15 mL acetonitrile. The resulting purple solution is stirred for 12 hrs. The solvent is then evaporated in a vacuum and compound 26 is purified by means of chromatography on alumina, the eluent being dichloromethane. The purple strip which is evaporated in a vacuum is collected. The slow diffusion of diethyl ether in a solution of the residue obtained after this final operation in CH$_2$Cl$_2$:MeCN (1:1) makes it possible to obtain 26 in the form of purple crystals with a yield of 53% (0.064 g)

$^1$H-NMR (CD$_3$CN) δ: 9.33 (ddd, 1H, H6' $^3$J=5.3, $^4$J=1.5, $^5$J=0.7), 8.44 (d, 1H, H3' $^3$J=8.2), 8.31 (d, 1H, H6" $^3$J=7.9), 8.18 (ddd, 1H, H6 $^3$J=5.6, $^4$J=1.5, $^5$J=0.6), 8.08 (ddd, 1H, H4' $^3$J=9.15, $^3$J=7.6, $^4$J=1.5), 7.79 (m, 2H, H5" and H4), 7.73 (ddd, 1H, H5' $^3$J=7.5, $^3$J=5.2, $^4$J=1.1), 7.17 (ddd, 1H, H5 $^3$J=7.3, $^4$J=1.4), 7.07 (m, 1H, H4"), 6.92 (m, 2H, H3 and H3"), 3.40 (q, 1H, CH $^3$J=6.6), 2.41 (s, 3H, CH$_3$CN), 2.04 (s, 3H, NCH$_3$), 1.96 (s, 3H, CH$_3$CN), 1.49 (s, 3H, NCH$_3$), 1.18 (d, 3H, CH$_3$ $^3$J=6.7). Anal. Calc. for $C_{24}H_{28}N_5F_6PRu$: C, 45.57, H, 4.46; N, 11.07. Found: C, 45.59, H, 4.51; N, 10.93.

Compound 27 is obtained in the same way by substituting (R) (1,1-phenylethyldimethylamine) by (S) (1,1-phenylethyldimethylamine).

Synthesis of Compound 28

1,2-bis,diphenylphosphinoethane $((P(C_6H_5)_2CH_2CH_2P(C_6H_5)_2)$ (0.141 g, 0.35 mmol) is added to a solution of compound 8 (0.2 g, 0.35 mmol) in methanol (30 mL). This yellow solution is stirred and heated under reflux of methanol for 19 hrs. The methanol is then evaporated in a vacuum and compound 28 is purified by chromatography on alumina, the eluent being CH$_2$Cl$_2$. The yellow fraction is collected, concentrated in a vacuum, the addition of diethyl ether bringing about the precipitation of the expected product which is then washed three times with ethylic ether (yield 46%, 0.143 g).

$^1$H-NMR (CD$_3$CN) δ: 8.94 (m, 1H, H6), 8.07 (d, 1H, H12 $^3$J=8.2), 7.95-7.84 (m, 3H, H9, H3 and H10), 7.64-7.36 (m, 20H, PPh$_2$), 7.07-7.01 (m, 2H, H5 and H4), 6.88 (ddd, 1H, $^3$J=7.3, H11 $^3$J=6.0, $^4$J=1.3), 2.69 (m, 4H, CH$_2$), 1.50 (d, 6H, $^5$JH-P=1.1 Hz, CH$_3$CN).

$^{31}$P-NMR (CD$_3$CN) δ: 68.41 (s, PPh$_2$), 43.64 (s, PPh$_2$), -143.3 (sept, PF$_6$).

Synthesis of Compound 29

Triphenylphosphine (0.186 g, 0.71 mmol) is added to a solution of compound 8 (0.2 g, 0.35 mmol) in methanol (30 mL). This yellow solution is stirred and heated under reflux of methanol for 72 hrs. The methanol is then evaporated in a vacuum and compound 29 is purified by chromatography on alumina, the eluent being CH$_2$Cl$_2$. The yellow fraction is collected and dried in a vacuum. The resulting solid is dissolved in a mixture of CH$_2$Cl$_2$:MeCN (1:1) to which the addition of diethyl ether brings about the crystallisation of 29 (yield 37%, 0.131 g).

$^1$H-NMR (CD$_3$CN) δ: 7.95 (dd, 1H, H6 $^3$J=5.9, $^4$J=0.7), 7.52 (m, 1H, H12), 7.4-7.0 (m, 33H, o, m, p PPh$_3$, H10, H9 and H3), 6.75 (ddd, 1H, H5 or H4 $^3$J=8.2, $^3$J=7.9), 6.67 (ddd, 1H, H4 or H5 $^3$J=8.1, $^4$J=1.5), 6.47 (ddd, 1H, H11 $^3$J=8.1), 2.14 (s, 3H, CH$_3$CN), 1.96 (s, 3H, CH$_3$CN).

$^{31}$P-NMR (CD$_3$CN) δ: 35.3 (s, PPh$_3$), -143.4 (sept, PF$_6$).

Anal. Calc. for $C_{51}H_{44}N_3F_6P_3Ru$: C, 60.83, H, 4.40; N, 4.17. Found: C, 61.15, H, 4.54; N, 4.46.

2. Test for the Proliferation of the Compounds According to the Invention on Tumoral Cell Lines Cells The products are tested on different cell lines. The cells used are RDM4 from a murine T lymphoma and a MOLT-4 line originating from an acute lymphoblastic leukemia. These cancer lines both express the p53 protein, unlike the HL-60 cells from a human promyelocytary leukemia where, following deletion of its gene, p53 is absent.

The influence of the p53 protein upon the effects induced by the products was determined by using the human lymphoblastoid line TK6 (p53 wild-type) and its NH32 variant of which the p53 gene was totally inactivated by double homologous recombination (Chuang et al, 1999). The TK6 cells originate from the American Tissue Culture Collection (ATGC, Manassas, Va., USA). The NH32 cells were supplied by H. L. Liber (Chuang et al, 1999).

All of these cells are cultivated in RPMI 1640-Glutamax, supplemented by 10% calf foetal serum heat inactivated at 56° C. for 30 minutes, 1 mM sodium pyruvate, 1 mM non-essential amino acids and 50 μg/mL gentamycine (Life Technologies, Cergy Pontoise, France). The cultures are kept in an incubator at 37° C. with a moisture saturated atmosphere, with 5% CO$_2$.

The concentration and viability of the cells are determined by the Trypan blue exclusion test (Sigma-Aldrich, France) and the cell density is maintained at a concentration of less than 10$^6$ cells/mL.

Proliferation Test

This test uses the UptiBlue reagent (Interchim, Montluçon, France), metabolised by the living cells. The cells are incubated on plates with 96 wells with 10$^4$ cells/well (200 μL) with the product and cultivated for 72 hours. Then, 20 μL UptiBlue are added to each well. After 3 hours incubation, the fluorescence of the samples contained in the plates is measured at 590 nm (excitation at 560 nm), using a Fluorolite 1000 microplate reader (Dynex technologies, Issy-Les-Moulineaux, France).

Results

The results are summarised in Table 1 below.

TABLE 1

| Ruthenium compounds | IC50 (µM) RDM4 line |
|---|---|
| 1 | 40 |
| 2 | — |
| 3 | — |
| 4 | 50 |
| 5 | 40 |
| 6 | — |
| 8 | >50 |
| 9 | 12 |
| 10 | >50 |
| 11 | 11 |
| 12 | 9 |
| 13 | 11 |
| 14 | 15 |
| Cisplatinum | 0.3 |

Compound 9 on other cell lines gives the following IC50: 9 (NH32):3; 9 (Molt-4):3.8; 9 (WTK1): 3; 9 (U-937): 3.
RDM4: lymphoma, mouse AKR
TK6: human lymphoblastoid line
NH32: TK6 variant, not expressing p53 ("p53 knock-out")
WTK1: other TK6 variant, expressing a p53 mutated gene
MOLT-4: human T lymphoblastic leukemia
U-937: human promonocyte leukemia Proliferation Test for the RDM4 Line with each Compound The potential anti-cancers are first of all selected on the RDM4 line. The effect of the different organo-ruthenium compounds upon the cell viability is firstly determined by a proliferation test as a function of the product concentration. The activity of the compounds derived from Ru is compared to that of cisplatinum. The exposure of the RDM4 cells to these derivatives is translated by a dose-dependent reduction in their proliferation. Therefore, the effect is dependent upon the organic complex which surrounds the Ru nucleus. The inhibition concentration of the growth of 50% of the cells (IC50) is determined for each of the products. Of all of the compounds tested, compounds 9 and 11 appear to be the most active with an IC50 of between 10 and 15 µM. The ruthenium derivatives showing an excessive IC50 (>50 µM) were eliminated from the biological study.

Measuring Apoptosis by Marking with Annexin-V on RDM4 Treated with Complexes 9 and 11

Cell death is measured by a first specific marking of the apoptosis. The externalisation of the anionic phospholipids, normally located on the inner layer of the plasmic membrane, is one of the precocious markers of apoptosis (Martin et al, 1996). Annexin-V is a protein which fixes specifically onto the phosphatidylserines in the presence of calcium. When Annexin-V is coupled to a fluorochrome, it makes it possible to quantify the apoptotic cells by flux cytometry.

The cells are marked after 24 hrs, 48 hrs and 72 hrs treatment with products 9 and 11 with two different concentrations: IC50 (15 µM) and a greater concentration which guarantees significant inhibition of proliferation (45 µM). The control cells are treated with the equivalent volume of solvent (ethanol). Treatment with 15 µM product does not shown any effect. After 72 hrs, the apoptosis rate is still as low as that of the control cells. On the other hand, with treatment at 45 µM, this rate already reaches 70% at 24 hrs and exceeds 99% after 48 hrs—a sign of significant apoptosis induction.

Measuring DNA Fragmentation by Marking with Propidium Iodure on RDM4s Treated with Complexes 9 and 11

A second specific marking of apoptosis is the fragmentation of DNA between the nucleosomes. The fragmented DNA is located in the apoptotic bodies in the terminal phase of apoptosis. This DNA is hypodiploid and so less in quantity than that present in normal cells. It can be quantified by flux cytometry after permeabilisation of the cell membranes and marking with PI. The quantity of DNA in a normal cell is 2n in the G0/G1 phase and 4n in the G2 phase. Therefore, the sub-G0 DNA in a quantity of less than 2n has a weaker fluorescence intensity.

The cells treated with 15 µM of product show an accumulation in the G0/G1 phase over the first two days of the experiment. This phenomenon tends to diminish after 48 hrs of treatment. On the other hand, when the cells are treated with 45 µM, the formation of hypodiploid particles, visualised by the sub-G0 DNA content, is less than 10% at 24 hrs and exceeds 50% at 48 hrs such as to reach 60% at 72 hrs. Fragmentation of the DNA shows that apoptosis induced by the products comes about rapidly. The quantity of hypodiploid particles in the control cells remains less than 4% over this same period.

The two organoruthenium complexes having an antiproliferative effect are capable of accumulating the RDM4 cells in the G0/G1 phase, but also of generating their apoptosis rapidly with a greater concentration—a sign of dose-dependant toxicity.

3. Apoptosis and Protein P53

The role of the p53 protein is central in the management of apoptosis and the induction of cell blockage. In the event of altering the cells' DNA, this protein is a transcriptional factor which regulates the expression of other proteins intervening in the blockage of the cycle, the repair of the DNA and in the induction of apoptosis (Alarcon-Vargas & Ronai, 2002).

Compared Effects of Complex 11 and of Cisplatinum upon the Proliferation of the MOLT-4 and HL-60 Lines The MOLT-4 cells possess the p53 gene which is suppressed by deletion in HL-60. The compared results of the proliferation tests show that product 11 and cisplatinum have different incidences upon the proliferative activity of these lines. Cisplatinum reduces the proliferation of MOLT-4 cells more significantly, (IC50<0.5 µM) than that of the p53-deficient HL-60 (human promyelocyte leukemia) (IC50=1 µM). This sensitivity is reversed with the Ru complex. The growth inhibition induced by Ru is more significant for HL-60s than for MOLT-4s. These latter, which have a normal p53 gene, are less sensitive to the Ru complex. The difference in proliferation in the presence of cisplatinum could be explained by a delay in the triggering of apoptosis in the HL-60 cells in relation to the MOLT-4 cells with activation of an independent secondary pathway of the p53 protein (Coelho et al, 2002). In the case of treating using organoruthenium product 11, this sensitivity variation can be attributed to the p53 status in the cell or to the difference of the cell type.

Compared Effects of Complex 11 and of Cisplatinum upon the Proliferation of Lines TK6 and NH32

The role of the p53 protein in cell proliferation in the presence of complex 11 and of cisplatinum is also studied on other cell lines: the TK6 human lymphoblastoid cells (p53 wild-type) and their NH32 variants (p53−/−). The proliferation curves of the two cell types can be superposed. The variation in the status of the p53 protein does not seem to have any effect upon the antiproliferative action of the Ru complex. On the other hand, cisplatinum brings about a more significant effect upon the p53+/+ cells than upon the p53-deficient cells. Therefore, p53 plays a role in the inhibiting capability of cisplatinum. However, the anti-proliferative action of cisplatinum is less significant than that of complex 11.

Measuring Apoptosis by Marking with Annexin-V on TK6 and NH32 Cells Treated with Complex 11

The toxicity of the organoruthenium complex on the TK6 and NH32 lymphoblastoid cells is measured with Annexin-V—a specific marker of precocious apoptosis. This marking is implemented on cells treated with derivative 11 at 1.5 µM after 0 hrs, 24 hrs, 48 hrs, 72 hrs and 96 hrs. The results show that the externalisation of the phosphatidylserines exceeds 50% at 48 hrs and reaches 90% after 72 hrs of continuous treatment. Beyond 72 hrs, the apoptosis reaches the maximum limit of 90% and forms a plateau. In the control cells, the apoptosis rate remains less than 10% for the whole of the experiment. The increase over time of the externalisation of the anionic phospholipids is similar in the two cell lines, but the TK6 cells enter into apoptosis with a delay of a dozen hours on their p53-deficient variants. The NH32 line reaches the limit formed by the 90% plateau earlier than the TK6 cells. The p53 protein seems to slow down activation of the precocious signs of apoptosis induced by the Ru complexes.

4. Chemo-Radiotherapeutic Association

The IC50s of the cisplatinum and of the organoruthenium 11 complex measured on the RDM4s are respectively approximately 0.7 µM and 15 µM. Cells of this same line are treated with concentrations of 0.7 µM cisplatinum and 15 µM complex 11. 24 hours after the start of the treatment, the cells are irradiated at 4 Gy with rapid neutrons. The effects of the chemo-radiotherapeutic association are then determined by simple cell counting, measuring the concentration of cells in the medium during treatment 24 hrs, 72 hrs and 168 hrs after irradiation.

The non-irradiated, treated and untreated samples all have an exponential proliferation. This growth is slowed down by adding organometallic chemical complexes. Cisplatinum at 0.7 µM inhibits proliferation more effectively than the ruthenium derivative at 10 µM. The chemo-radiotherapeutic association increases the efficiency of the chemical compounds and shows an effect greater than a simple addition of the effects of ionising radiation and complexes taken separately. The curve of ruthenium derivative 11 on its own is superposed on that of the control cells. The antiproliferative effect of this complex at this concentration is negligible. But the addition of ionising radiation to this product involves a radical effect making the cell proliferation practically zero for the duration of the experiment. This observation is not found to such a significant extent with cisplatinum which, when used on its own, has a more marked cytostatic effect than that of complex 11.

Evaluation of the effects of a combined "ionising radiation+RDC-11" treatment upon proliferation and survival of the RDM4 murine cells. These cells originate from an AKR mouse lymphoma. The different tests were carried out in vitro, and five independent experiments were carried out.

The radiations used were rapid neutrons originating from the collision of 65 MeV protons on a Beryllium target (produced at the Cyclotron, Louvain la Neuve (LLN) in Belgium). The results of just one of these experiments which is representative of a set of three experiments carried out with this type of radiation are shown. Similar results were observed with X rays (produced at the Paul Strauss Centre, Strasbourg), and carbon ions (produced at GANIL, Caen).

Experimental Protocol

The RDM4 cells are adjusted to 50,000 cells/ml, in RPMI 1640 culture medium to which 10% foetal calf serum is added. 4 25 cm2 culture flasks are filled with cell suspension, at the rate of 10 ml/flask, i.e. 500,000 cells/flask.

Four flasks are prepared thus, each corresponding to a different experimental group:
Group 1: non-irradiated, untreated cells (Et/NI in FIG. 9)
Group 2: non-irradiated cells, treated with RDC-11 (RDC-11/NI in FIG. 9)
Group 3: irradiated, non-treated cells (Et/4 Gy in FIG. 9)
Group 4: irradiated cells, treated with RDC-11 (RDC-11/4 Gy in FIG. 9)

RDC-11, prepared from an ethanolic solution, is added to the cells (flask 2 and 4) 6 hours before irradiation. An identical volume of ethanol (Et, 66 µl) is added to flasks 1 and 3. The final concentration of RDC-11 is 10 µM, and the medium is not replaced over the 9 days of the experiment.

Flasks 3 and 4 are irradiated with 4 Gy, at ambient temperature, then returned to culture at 37° C.

On the days following irradiation, aliquots of cell suspensions are regularly taken. The number of cells is determined using a Coulter Counter. Other cells are fixed in ethanol, then marked with propidium iodure, in order to determined the percentage apoptosis.

Results

The cell counts clearly show up the action of the radiation and of the RDC-11 on the proliferation of the RDM4s. When these two treatments are combined, cell growth is significantly slowed down. This effect is particularly marked 9 days following irradiation (FIG. 9).

The analysis by flux cytometry of the cells marked with propidium iodure indicates, moreover, that the co-treatment induces more apoptosis than irradiation on its own, or than RDC-11 on its own, and that the percentage of cells in apoptosis is greater than the sum of treatments taken separately (FIG. 10).

Conclusions

Upon the basis of these two criteria, and starting with these results, it can be concluded that the RDC-11+irradiation combination has a supra-additive effect. Comparable results were obtained with X rays used by radiotherapy, and carbon ions. They were confirmed by means of other tests, such as MTT or Alamar Blue.

5. Analysis of the Cytostatic and Cytotoxic Effects of the Compounds Derived from Ruthenium on Glioblastoma and Neuroblastoma Cultures The first step towards characterising the anticancerous effects of the compounds derived from ruthenium consists of testing their activity on tumoral lines kept in culture and comparing these effects on lines which have different characteristics as regards resistance to the anticancer treatments. Two lines of human glioblastomas (A172, HS683) and two lines of neuroblastomas (N2A and SH5Y) were used in order to test the cytostatic effects of the compounds according to the invention. Cisplatinum was chosen as the cytotoxic comparison agent. In a first approach, an MTT test was used to measure the activity of a mitochondrial enzyme, and this gives an estimate of the number of cells. Then, the cytotoxic effects of the compounds according to the invention were characterised in greater detail by analysing the morphology of the nucleus and the activation of caspase 3—two markers of cell apoptosis.

Results

Several compounds derived from ruthenium reduce the number of tumoral cells and, and on all of the lines tested, A172, HS683, N2A, and SH5Y (FIG. 1, table 2). For the most active compounds (compounds 6, 9 and 12), this effect is observed at a concentration similar to or lower than that of cisplatinum. Using these experiments as a basis, IC50 values were estimated corresponding to the concentration necessary in order to reduce by half the quantity of tumoral cells present in relation to the control condition. These results summarised in table 1 were also reproduced in other cell lines, the HCT116s and the 293s, and on primary glial cultures.

The immunocytochemical analyses on A172 glioblastoma cells showed that after 48 hrs treatment, compounds 6, 9 and 12 induce nuclear condensation and fragmentation characteristic of apoptosis (FIGS. 2A, B). Moreover, the cells treated with the most active compounds (compound 6) show more significant marking of the active fragment of caspase 3 (FIGS. 2A, B). This result is reinforced by increasing the proteic levels of the active fragment of caspase 3 detected by Western blot in the A172 cells treated with cisplatinum or with a compound (compound 6 or 9, FIG. 2C). Equivalent results were also observed in the N2A and HCT116 cells (results not shown).

As a whole, the results show that the ruthenium compounds (6, 9 and 12) have cytostatic and cytotoxic effects upon the lines of neuroblastoma, glioblastoma and other cell types. The characterisation of the cytotoxic effects shows that these CDR induce apoptosis in these various cell types, in keeping with what is observed with cisplatinum.

6. Analysis of the Molecular Mechanisms used by the Ruthenium Derivatives

Stopping cell proliferation or inducing apoptosis are cell processes induced by various anticancer drugs. Two of the proteins which are important for triggering these processes are the proteins encoded by homologous genes p53 and p73 (Marin and Kaelin 2000). Proteins p53 and p73 encoded by these two genes are transcription factors of which the proteic levels are induced in response to damage to the DNA or other cellular stresses. Induction of the p53 proteic levels passes via an increase in the stability of the protein which is no longer degraded by the proteasome pathway (Vargas, Takahashi et al. 2003; Yang, Li et al. 2004). Cisplatinum is an inducer of p53 and p73 (Siddik 2003). Moreover, these proteins, as transcription factors, induce the expression of particular genes directly involved in stopping cell growth, such as p21— an inhibitor of the cyclin-dependent kinases, or in apoptosis, such as bax which is located in the mitochondria and is involved in the salting out of cytochrome C (Prives and Hall 1999).

For the purpose of determining the molecular mechanisms used by the ruthenium derivatives and comparing them with those induced by cisplatinum, the expression of p53, p73 p21 and bax in the A172 and HCT116 lines was analysed.
Results:

Western blot analyses were carried out in order to determine whether the CDR induce p53 proteic levels in A172 cells. The results show differences between the CDR and cisplatinum. After 24 hrs treatment, cisplatinum induces the p53 proteic levels, but no effect is observed for CDR 6 (FIG. 3). On the other hand, at 6 hrs treatment, CDR6 and cisplatinum induce p53. An equivalent result is observed on the p73 proteic levels.

In order to determine whether the induction of p53 and p73 proteins leads to activation of the target genes of these proteins, the expression of p21 and Bax was analysed by Western blot. After 24 hours treatment, CDR 6, like cisplatinum, induces the expression of p21 and Bax (FIG. 4).

These experiments were repeated in the HCT116 cells which are widely used as models for studying the activation of p53 by anticancer agents. In these cells, an induction of p53 by the CDR (CDR6) was also observed, but with certain differences (FIG. 5). On the one hand, the activation kinetics are similar to those of cisplatinum starting at 6 hrs and being maintained until 24 hrs. On the other hand, the CDR induce p53 more weakly than cisplatinum. However, the increase in the expression of p21 and inhibition of the phosphorylation of histone H3—a cell proliferation marker—are identical for CDR 6 and cisplatinum.

The data collected show that the CDR induce molecular mechanisms in part identical to those used by cisplatinum (p53, p73, Bax, p21). However, there are also differences which indicate that the CDR would trigger mechanisms different to those of cisplatinum or of other anticancer compounds.

7. Analyses of the Sensitivity of the Ruthenium Derivatives to the Cell Resistance Mechanisms The anticancer effects of drugs such as cisplatinum are unfortunately greatly reduced by the triggering by the cell of resistance processes which block apoptotic mechanisms (mutation of p53 . . . ) or increase the expression of proteins which detoxify the cell. For cisplatinum, several mechanisms have been described and they are also effective against carboplatinum, a derivative of cisplatinum (Safaei, Katano et al. 2004). It is therefore particularly important to test the sensitivity of the CDR with respect to these resistance mechanisms so as to determine the precise contribution which these compounds can make to the treatment of tumours which are resistant to the chemotherapy treatments which already exist.

One of these mechanisms is the overexpression of the copper export pump (ATP7B) which expels cisplatinum from the cell. It has been shown that this molecule is overexpressed in human tumours and that cell lines which overexpress this molecule are more resistant to cisplatinum and carboplatinum than control lines.
Results:

Two cell lines derived from 2008 cells (Katano, Safaei et al. 2003) were studied. One overexpresses the ATP7B pump, and the other only contains the control vector. The cytostatic activity of the cisplatinum and the CDR was tested in these two lines using the MTT test. Very interestingly, it was observed that the line expressing ATP7B is significantly less sensitive to cisplatinum, whereas its sensitivity with respect to CDR6 is equivalent to that of the control line (FIG. 5).

These results suggest that the resistance mechanisms developed by a cell against cisplatinum or against another drug are, in part, less effective against the CDR. It can therefore be considered to use CDR in the treatment of tumours which are resistant to cisplatinum or to other anticancer drugs.

8. Use of the Compounds Derived from Ruthenium in Combination with Other Anticancer Agents The mechanisms induced by various anticancer drugs are different according to the mode of action of these drugs. For numerous years, anticancer treatments combining several drugs have been used so as to increase their effectiveness. Using this approach as a basis, treatments combining ruthenium derivatives with other drugs such as NCS (Neocarzinostatin) and Taxol have been undertaken, and their effectiveness compared to that of individual treatments. NCS induces DNA double strand breaks, similar to those of gamma rays (Smith and Nicolaou 1996). Taxol disrupts the mitotic spindles (Oberlies and Kroll 2004).

Results:

NCS or Taxol are drugs with an IC50 similar to the nM. A comparison was made using two doses of NCS and two doses of Taxol. The one enables one to expect the IC50, the other leads to a reduction by 10% of the cell viability after 48 hrs treatment. These two concentrations were combined with a concentration of ruthenium derivative or cisplatinum bringing about 10% of the maximum effect. Co-treatment by the ruthenium derivatives (CDR 6) is significantly more effective in relation to a co-treatment with cisplatinum (FIG. 6). Equivalent results are obtained with Taxol and NCS.

These results show that the compounds derived from ruthenium have a "potentialising" effect which is significantly stronger than cisplatinum upon the activity of other drugs such as NCS or Taxol.

9. MTT Test

The experiments are carried out under a vertical laminar flow hood. The cell growth medium is made up of DMEM (Dulbecco's Modified Eagle's Medium), HEPES, 10% FCS (Foetal Calf Serum), 5% PS (Penicillin, Streptomycin) and is stored at +4° C., and PBS (Phosphate Buffer Saline, pH=7.4). Trypsin-EDTA (0.25% trypsin in 1 mM $Na_4$(EDTA)) and FCS are stored at −15° C. and defrosted before use. MTT (4,5-dimethylthiazol-2-diphenyltetrazolium bromide) is a yellow solid produced under the Aldrich brand. It is placed in sterile aqueous solution at a concentration of 5 mg/mL and kept at +4° C. It is diluted to 10% in a cell culture medium when used as a colouring agent for living cells.

The cancerous human cells of the colon (HCT-116) or of the liver (A-172) were bought from the European Type Culture Collection, and placed in an incubator at 37° C., 5% $CO_2$ in round Petri dishes (diameter 10 cm.) with 10 mL medium. When they are sufficiently numerous (70% confluence), they are washed in PBS at ambient temperature and then mixed with 1.5 mL Trypsin-EDTA in order to lift them from the Petri dish. They are placed in the incubator for several minutes so as to accelerate this detachment. This cell suspension is placed in culture medium heated to 37° C., then this solution is spread over cell culture plates with 96 wells (100 µL/well) which are left to incubate for 48 hours until 50% cell confluence is reached. The medium is renewed by cell medium containing different concentrations of RDCs and cisplatinum at 37° C., which is left to incubate. After 48 hours, the medium is replaced by a solution at 37° C. of MTT in medium which is placed in the incubator for at least one hour or until violet crystals from the complexation of the MTT are formed quantitatively at the bottom of each well. Finally, this medium is replaced by 100 µL/well of an HCl/$^i$PrOH 0.04 M solution at ambient temperature so as to dissolve the crystals. The optical density of the solutions obtained is read. The optical densities of the wells treated with RDCs or cisplatinum are compared with those in the untreated (control) wells. One manipulation consists of treating 4 plates (3×RDC and cisplatinum). Each plate contains a single product with different concentrations. 9 columns are treated at 50, 20, 15, 10, 7.5, 5, 2.5, 1 and 0.2 µM and 3 columns are left as controls. Only the control columns marked (i)m (1<i<4) (FIG. 11) are taken into account for the calculations.

Determination of the $IC_{50}$ and the statistical variance and Newmann-Keuls tests are carried out using Prism GraphPad v. 4 software.

The results on the MTT are given in FIG. 11 for the HCT-116.

A table summarising the $IC_{50}$ obtained is given below:

| Table summarising the $IC_{50}$ | | |
|---|---|---|
| $IC_{50}$ µM | A-172 | HCT-116 |
| RDC-17 | 5 | 5-7 |
| RDC-20 | 15 | 20-30 |
| RDC-24 | 10 | 1-5 |
| RDC-28 | | |
| RDC-29 | 15 | |

10. In Vivo Test

RDC-11 was tested in vivo in order to confirm its anticancer properties in vitro, as demonstrated above. A preliminary experiment carried out on a small number of healthy SWISS mice showed the lack of apparent toxicity of RDC-11.

The animals are manipulated under a laminar flow hood. Ten nude/nude (athymic) eleven week old SWISS mice were grafted subcutaneously with U-87 cells (a human glioblastoma) on the left thigh. After 7 days, the tumours become apparent and treatment commences. The animals are separated into two groups of five, 5 mice are thus treated with D-PBS (control mice) and the 5 others with RDC-11 (treated mice).

For the treated mice, 2 mg of RDC-11 placed in solution in 4 mL hot D-PBS for each injection. 0.5 mL of this solution cooled down to ambient temperature is administered intraperitoneally to each mouse. For the control mice, 0.5 mL D-PBS at ambient temperature is administered in the same way.

The injection days are marked with a cross in the table below:

| May 2005 | | | | | | |
|---|---|---|---|---|---|---|
| Sun | Mon | Tues | Wed | Thurs | Fri | Sat |
| 22 | 23 | X 24 | 25 | X 26 | 27 | 28 |
| 29 | X 30 | 31 | | | | |

| June 2005 | | | | | | |
|---|---|---|---|---|---|---|
| Sun | Mon | Tues | Wed | Thurs | Fri | Sat |
| | | | X 1 | 2 | X 3 | 4 |
| 5 | 6 | X 7 | X 8 | X 9 | X 10 | 11 |
| 12 | X 13 | 14 | 8 15 | 16 | 17 | 18 |

X = injection day
$ = mouse sacrifice

The dose of RDC-11 injected is 18.5 mg/Kg mouse. The accumulated dose is therefore 185 mg/Kg.

The development of the apparent tumours was followed by measuring them with calipers, by weighing the mice and by scanning one mouse from each batch with a CT-scan after injecting a contrast product (Fenestra VC). The mice were individualised by a mark on the ear.

The volume of the apparent tumours was calculated according to the formula:
$V=(4/3)*\pi*(L/2)*(I/2)^2$ where L is the length and I the width measured.

FIGS. 12 and 13 show the development of the volumes of the apparent tumours and of the weights of the mice over time.

When the mice are dissected, the tumours in the two groups are isolated and weighed (in g). The results are given in FIG. 14. By comparing the figures showing the tumour measurements (calculated volume and weight), it is possible to conclude that the volumes of the tumours calculated are smaller than the volumes of the tumours observed. In fact, the tumours have grown depth-wise, hence the difficulty in measuring them with calipers. Nevertheless, the weight and the volume of the treated tumours are less in relation to the controls.

Conclusions

RDC-11 changes the nature of tumoral growth without any toxicity.

References

Alarcon-Vargas D. & Ronai Z. (2002). p53-Mdm2—the affair that never ends. *Carcinogenesis*. 23(4), 541-7

Coelho D, Fischer B, Holl V, Jung G M, Dufour P, Bergerat J P, Denis J M, Gueulette J, Bischoff P. (2002). involvement of tp53 in apoptosis induced in human lymphoblastoid cells by fast neutrons. Radiat. Res. 157(4), 446-52

Katano, K., R. Safaei, et al. (2003). "The copper export pump ATP7B modulates the cellular pharmacology of carboplatin in ovarian carcinoma cells." *Mol Pharmacol* 64(2): 466-73.

Marin, M. C. and W. G. Kaelin, Jr. (2000). "p63 and p73: old members of a new family." *Biochim Biophys Acta* 1470(3): M93-M100.

Oberlies, N. H. and D. J. Kroll (2004). "Camptothecin and taxol: historic achievements in natural products research." *J Nat Prod* 67(2): 129-35.

Prives, C. and P. A. Hall (1999). "The p53 pathway." *J Pathol* 187(1): 112-26.

Safaei, R., K. Katano, et al. (2004). "Cross-resistance to cisplatin in cells with acquired resistance to copper." *Cancer Chemother Pharmacol* 53(3): 239-46.

Siddik, Z. H. (2003). "Cisplatin: mode of cytotoxic action and molecular basis of resistance." *Oncogene* 22(47): 7265-79.

Smith, A. L. and K. C. Nicolaou (1996). "The enediyne antibiotics." *J Med Chem* 39(11): 2103-17.

Vargas, D. A., S. Takahashi, et al. (2003). "Mdm2: A regulator of cell growth and death." *Adv Cancer Res* 89: 1-34.

Yang, Y., C. C. Li, et al. (2004). "Regulating the p53 system through ubiquitination." *Oncogene* 23(11): 2096-106.

The invention claimed is:

1. A pharmaceutical composition comprising, in a pharmaceutically acceptable support, at least one complex ruthenium compound (II) with the following general formula (I) or (II):

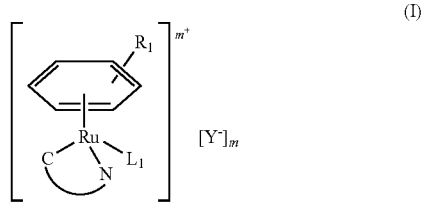

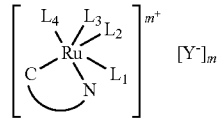

formula (I) or (II) in which:

$L_1$, $L_2$, $L_3$ and $L_4$, identical or different, represent a donor ligand with 2 electrons to one nitrogen, oxygen, phosphorus or sulphur atom, R1 represents a hydrogen atom or one or more substitutions on the phenyl group, chosen from a (C1-6)alkyl and (C6-18)aryl radical, Y is a counter-ion (when m =1), m is 0 or 1, between C and N, represented by a curved line, there is a series of atoms forming, with the carbon, nitrogen and ruthenium atoms shown in formulae (I) and (II), the metallocycle, which is formed by between 5 and 8 atoms (including the carbon, nitrogen and ruthenium atoms shown in formulae (I) and (II)), wherein the atoms of the series of atoms are selected from the group consisting of carbon, nitrogen, oxygen and sulphur atoms.

2. The composition according to claim 1, wherein the donor ligands with two electrons to one nitrogen, oxygen, phosphorus or sulphur atom are chosen from $H_2O$, $di((C_{1-6})alkyl)O$, $di((C_{1-6})alkyl)S$, $di((C_{1-6})alkyl)S(O)$, $(C_{1-6})alkyl)SO_3^-$, $di((C_{1-6})alkyl)C=O$ et $(C_{1-6})alkylCO_2^-$.

3. The composition according to claim 1, wherein the donor ligands with two electrons to one nitrogen atom are chosen from the ligands with the formula $(C_{1-6})alkylCN$ (in particular $CH_3CN$) and pyridine ligands, possibly substituted, on one or more carbon atoms from the pyridine cycles, by a $(C_{1-6})alkyl$ radical or a halogen atom.

4. The composition according to claim 1, wherein the donor ligands with two electrons to one nitrogen atom are chosen from the primary $(C_{1-6})alkyl$ amines such as methylamine or ethylamine.

5. The composition according to claim 1, wherein the donor ligands with two electrons to one phosphorous atom are ligands of the phosphine type.

6. The composition according to claim 1, wherein the donor ligands with two electrons to one phosphorus atom have the formula
$P(Ph)_{3-x}(alkyl)_x$, with x representing 0, 1 or 2.

7. The composition according to claim 1, in the case of formula (II), wherein at least two of the $L_1$, $L_2$, $L_3$ and $L_4$ groups, taken two by two, are linked by at least one covalent bond.

8. The composition according to claim 1, in the case of formula (II), wherein at least two of the $L_1$, $L_2$, $L_3$ and $L_4$ groups, taken two by two, represent the bipyridine or phenanthroline motifs, possibly substituted, in particular by at least one alkyl radical, or else by 1,2-bisdiphenylphosphinoethane.

9. The composition according to claim 1, in the case of formula (II), wherein at least one $L_1$, $L_2$, $L_3$ and $L_4$ group representing a donor ligand with two electrons to one nitrogen or phosphorus atom, is a pyridine, phosphine, bipyridine or phenanthroline group.

10. The composition according to claim 1, in the case of formula (II), wherein at least two of the $L_1$, $L_2$, $L_3$ and $L_4$ groups represent nitrile ligands, such as, for example, ligands with the formula $(C_{1-6})alkylCN$ (in particular $CH_3CN$).

11. The composition according to claim 1, in the case of formula (II), wherein two of the $L_1$, $L_2$, $L_3$ and $L_4$ groups represent nitrile ligands, such as for example ligands with the formula $(C_{1-6})$alkylCN (in particular $CH_3CN$), and the two other ligands are linked by at least one covalent bond.

12. The composition according to claim 1, wherein $Y^-$ is $PF_6^-$, $BF_4^-$, $CF_3CO_2^-$, $CH_3CO_2^-$, $CF_3SO_3^-$, or $NO_3^-$.

13. The composition according to claim 1, wherein m is equal to 1.

14. The composition according to claim 1, wherein the curved line is a metallocycle with 5 atoms chosen from a metallocycle defined according to any of the following formulae:

(1)
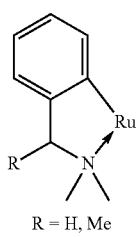
R = H, Me (2)
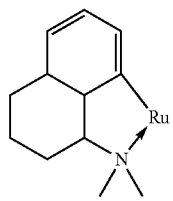

(3)
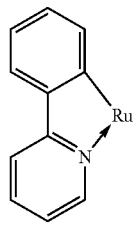

(4)
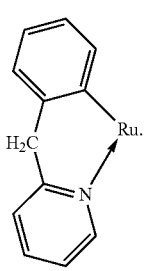

15. The composition according to claim 1, wherein the curved line is a metallocycle with 6 or 7 atoms chosen from a metallocycle defined according to either of the following formulae:

(5)
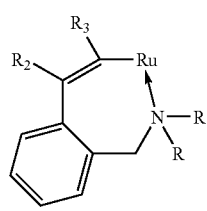

(6)
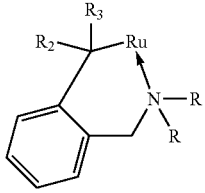

with R, identical or different, representing H or an alkyl radical, preferably methyl, and $R_2$ and $R_3$, identical or different, representing a hydrogen atom, a halogen atom, an alkyl group, an alkoxy, thiol, thioether, hydroxyl, nitro, cyano or ester radical.

16. The composition according to claim 1, wherein the compound is chosen from compounds 5 to 6 and 8 to 29:

5
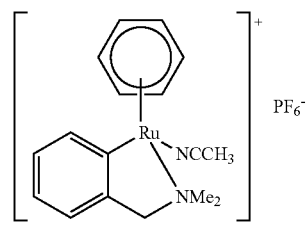

6
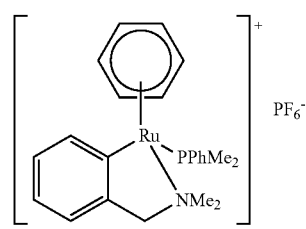

8
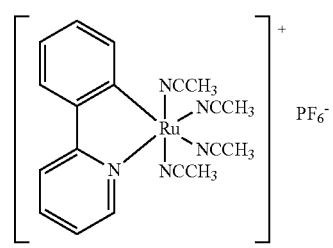

9
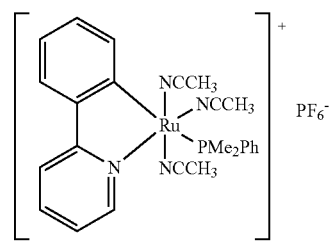

| 10 | 16 |
|---|---|
| 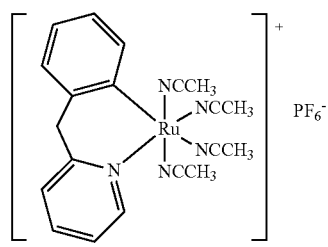 | 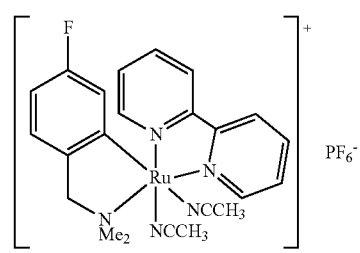 |
| 11 | 17 |
| 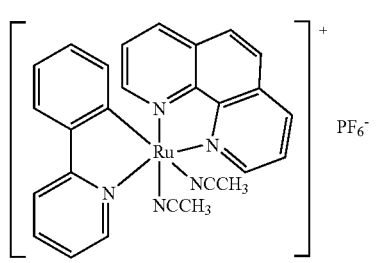 | 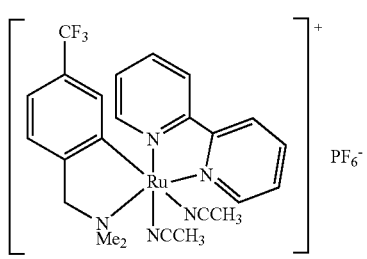 |
| 12 | 18 |
| 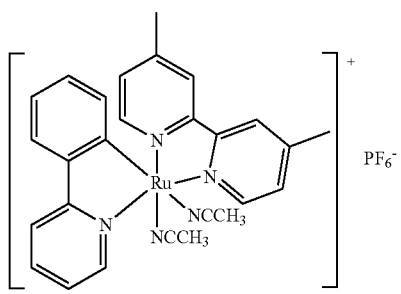 | 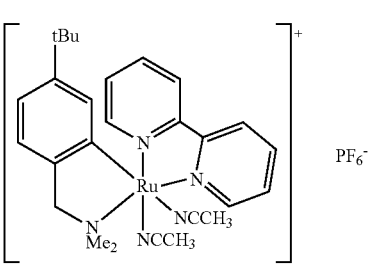 |
| 13 | 19 |
| 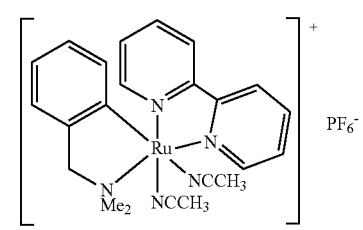 | 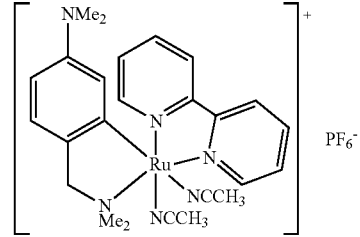 |
| 14 | 20 |
| 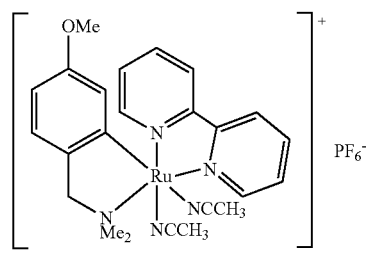 | 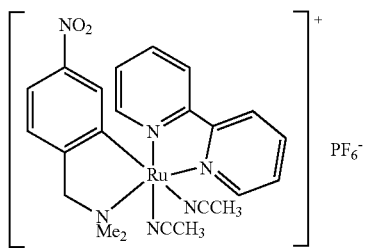 |
| 15 | 21 |
| 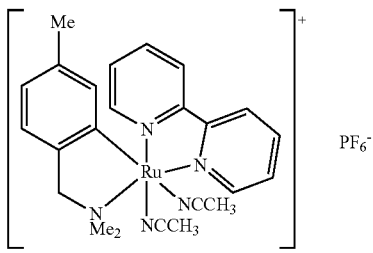 | 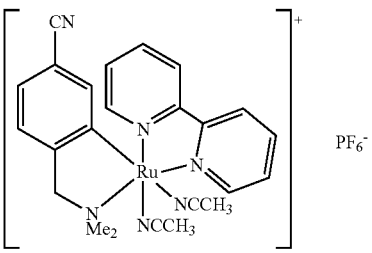 |

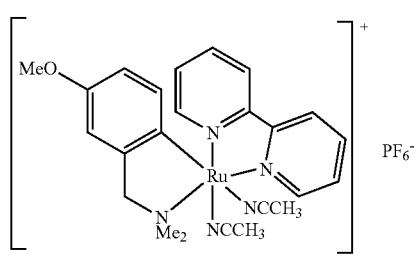
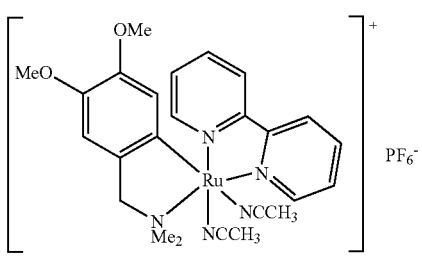
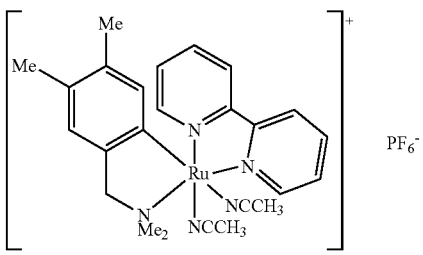
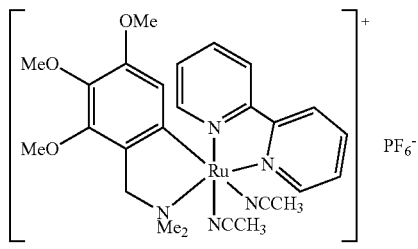
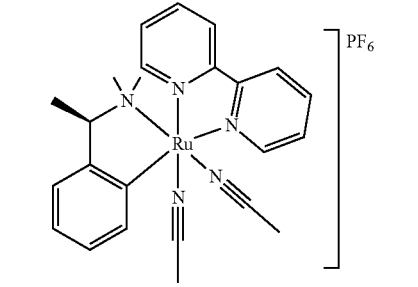
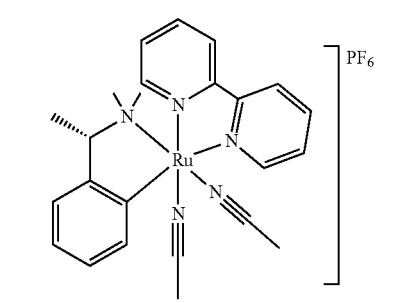
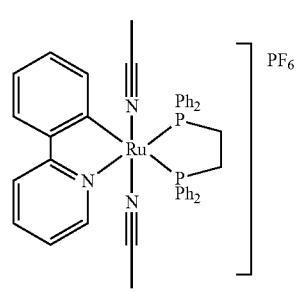
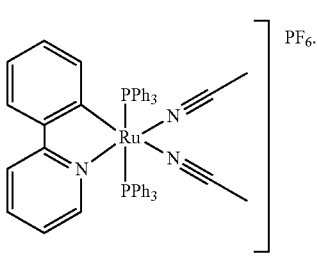
17. A ruthenium compound, chosen from the following compounds:
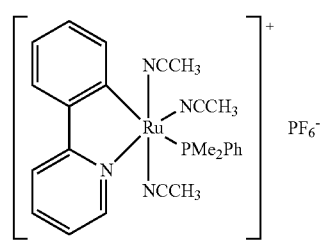
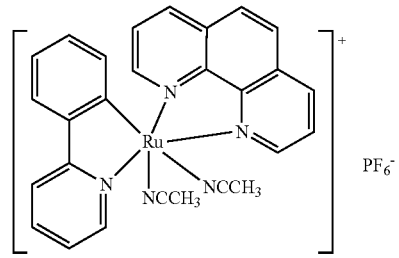
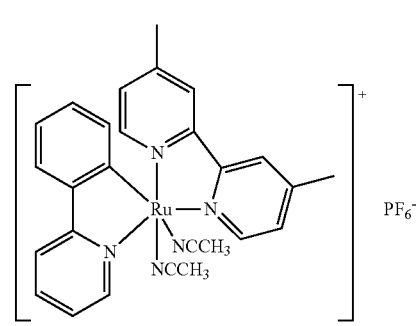

14
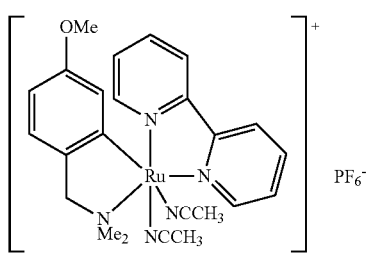
15
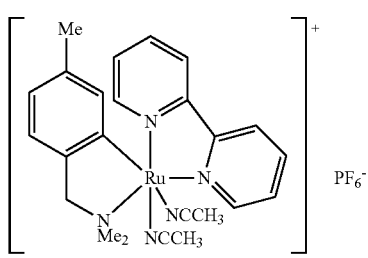
16
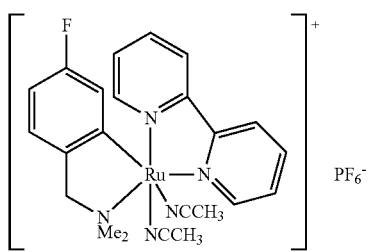
17
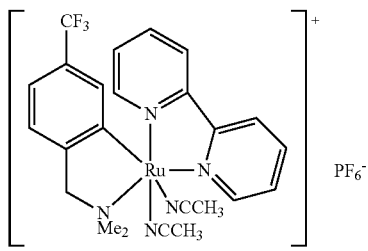
18
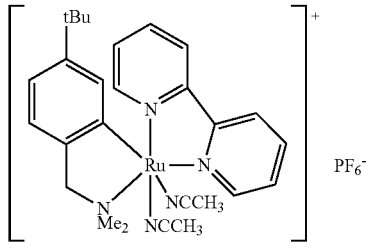
19
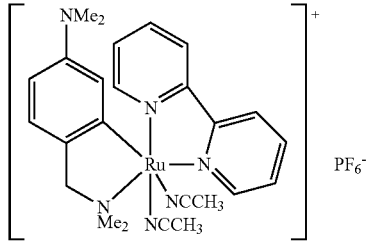
20
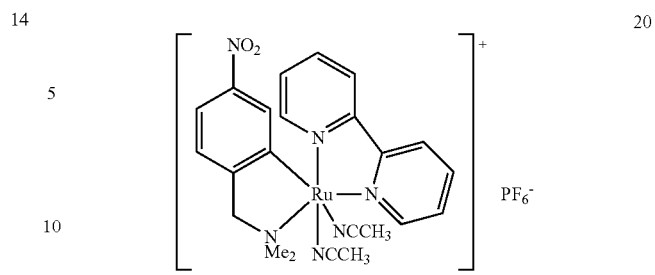
21
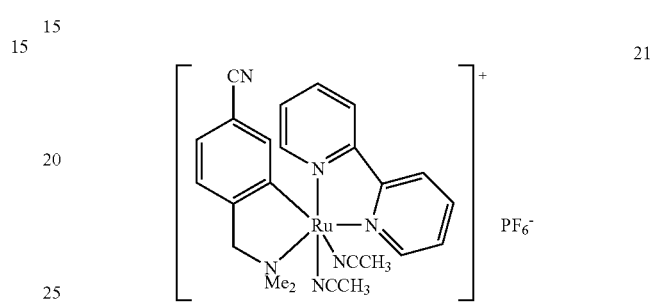
22
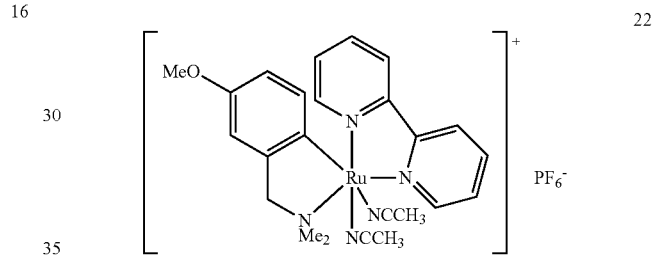
23
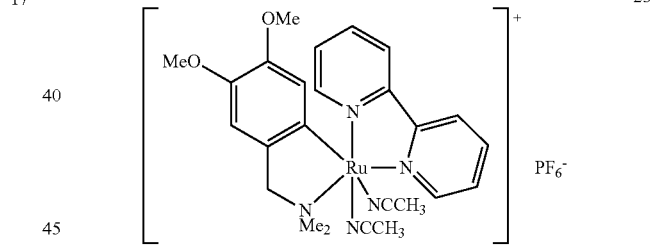
24
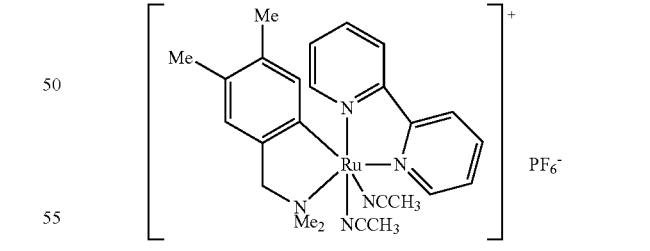
25
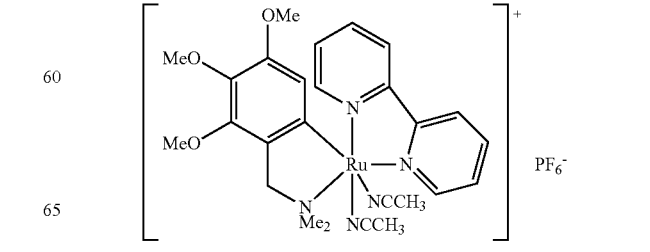

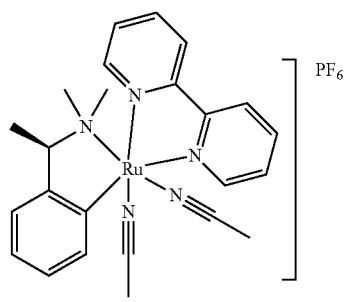

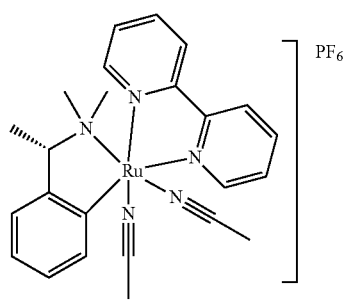

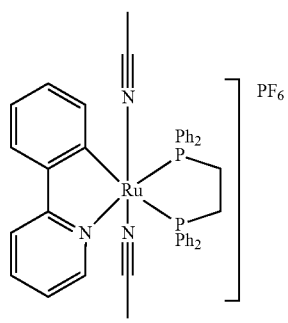

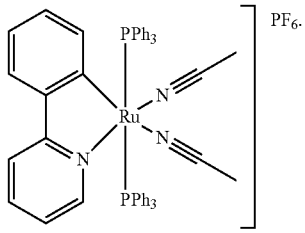

18. The composition according to claim 1, for treating neuroblastomas, glioblastomas, (promyelocytary) leukemias, cancers of the prostate, the ovaries, the lungs, the breasts, the liver, the pancreas, the head, the neck, the central nervous system, renal cancers, gastric cancers or melanomas.

19. The composition according to claim 1, for treating neuroblastomas, glioblastomas, (promyelocytary) leukemias, cancers of the prostate, the ovaries, the lungs, the breasts, the liver, the pancreas, the head and neck, the colon, the central nervous system, renal cancers, gastric cancers or melanomas by accumulating the tumoral cells in the G0/G1 phase, and possibly by inducing apoptosis.

20. The composition according to claim 1, for treating neuroblastomas, glioblastomas, (promyelocytary) leukemias, cancers of the prostate, the ovaries, the lungs, the breasts, the liver, the pancreas, the head and neck, the colon, the central nervous system, renal cancers, gastric cancers or melanomas which are resistant to cisplatinum or to other anticancer drugs.

21. The composition according to claim 1, for treating neuroblastomas, glioblastomas, (promyelocytary) leukemias, cancers of the prostate, the ovaries, the lungs, the breasts, the liver, the pancreas, the head and neck, the colon, the central nervous system, renal cancers, gastric cancers or melanomas in combination with an anti-cancer treatment implementing radiation, such as radiotherapy and brachytherapy.

22. The composition according to claim 1, for treating neuroblastomas, glioblastomas, (promyelocytary) leukemias, cancers of the prostate, the ovaries, the lungs, the breasts, the liver, the pancreas, the head and neck, the colon, the central nervous system, renal cancers, gastric cancers or melanomas in combination with at least one other chemical anti-cancer agent, conditioned and administered in combination, separately or sequentially.

23. The pharmaceutical composition comprising, in a pharmaceutically acceptable support, at least one compound as defined in claim 17.

* * * * *